US009883914B2

(12) United States Patent
Larkin et al.

(10) Patent No.: US 9,883,914 B2
(45) Date of Patent: *Feb. 6, 2018

(54) ROBOTIC SURGERY SYSTEM INCLUDING POSITION SENSORS USING FIBER BRAGG GRATINGS

(71) Applicant: Intuitive Surgical Operations, Inc., Sunnyvale, CA (US)

(72) Inventors: David Q. Larkin, Menlo Park, CA (US); David C. Shafer, Menlo Park, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/813,944

(22) Filed: Jul. 30, 2015

(65) Prior Publication Data

US 2015/0374453 A1     Dec. 31, 2015

Related U.S. Application Data

(63) Continuation of application No. 13/049,003, filed on Mar. 16, 2011, now Pat. No. 9,125,679, which is a
(Continued)

(51) Int. Cl.
*A61B 19/00* (2006.01)
*B25J 19/02* (2006.01)
(Continued)

(52) U.S. Cl.
CPC .............. *A61B 34/30* (2016.02); *A61B 34/20* (2016.02); *A61B 34/37* (2016.02); *A61B 34/71* (2016.02);
(Continued)

(58) Field of Classification Search
None
See application file for complete search history.

(56) References Cited

U.S. PATENT DOCUMENTS 3,096,962 A     7/1963   Meijs
3,546,961 A    12/1970   Marton
(Continued)

FOREIGN PATENT DOCUMENTS

CN    1155833 A     7/1997
CN    1486667 A     4/2004
(Continued)

OTHER PUBLICATIONS

Abbott, Daniel J. et al., "Design of an Endoluminal Notes Robotic System," Conference on Intelligent Robots and Systems, 2007, pp. 410-416.
(Continued)

*Primary Examiner* — Mussa A Shaawat
*Assistant Examiner* — Kyung Kim

(57) ABSTRACT

An apparatus comprises a robotic manipulator and a surgical instrument mounted to the robotic manipulator. The surgical instrument comprises an elongate arm including an actively controlled bendable region including at least one joint region and an end effector and a passively bendable region including a distal end coupled to the actively controlled bendable region. An actuation mechanism extends through the passively bendable region and is coupled to the at least one joint region to control the actively controlled bendable region. A channel extends through the elongate arm, and an optical fiber is positioned in the channel. The optical fiber includes an optical fiber bend sensor in at least one of the passively bendable region or the actively controlled bendable region.

20 Claims, 10 Drawing Sheets

US 9,883,914 B2

Page 2

Related U.S. Application Data continuation of application No. 11/491,384, filed on Jul. 20, 2006, now Pat. No. 7,930,065.

(60) Provisional application No. 60/755,157, filed on Dec. 30, 2005.

(51) Int. Cl.
| | |
|---|---|
| B25J 9/16 | (2006.01) |
| B25J 18/06 | (2006.01) |
| A61B 34/30 | (2016.01) |
| A61B 34/00 | (2016.01) |
| A61B 90/30 | (2016.01) |
| A61B 34/37 | (2016.01) |
| A61B 17/00 | (2006.01) |
| A61B 17/29 | (2006.01) |
| A61B 17/04 | (2006.01) |
| A61B 34/20 | (2016.01) |
| A61B 90/00 | (2016.01) |

(52) U.S. Cl.
CPC ............. *A61B 90/30* (2016.02); *B25J 9/1635* (2013.01); *B25J 18/06* (2013.01); *B25J 19/025* (2013.01); *A61B 90/361* (2016.02); *A61B 2017/00057* (2013.01); *A61B 2017/00477* (2013.01); *A61B 2017/0477* (2013.01); *A61B 2017/2906* (2013.01); *A61B 2034/2048* (2016.02); *A61B 2034/2059* (2016.02); *A61B 2034/2061* (2016.02); *A61B 2034/2065* (2016.02); *A61B 2034/305* (2016.02); *A61B 2090/3614* (2016.02); *Y10S 901/09* (2013.01); *Y10S 901/28* (2013.01); *Y10S 901/46* (2013.01); *Y10S 901/47* (2013.01); *Y10T 29/49826* (2015.01); *Y10T 74/20305* (2015.01)

(56) References Cited

U.S. PATENT DOCUMENTS

| | | |
|---|---|---|
| 4,437,114 A | 3/1984 | Larussa |
| 4,792,715 A | 12/1988 | Barsky et al. |
| 4,809,191 A | 2/1989 | Domeier et al. |
| 4,949,927 A | 8/1990 | Madocks et al. |
| 5,114,403 A | 5/1992 | Clarke et al. |
| 5,174,276 A | 12/1992 | Crockard |
| 5,251,611 A | 10/1993 | Zehel et al. |
| 5,297,536 A | 3/1994 | Wilk |
| 5,307,437 A | 4/1994 | Facq et al. |
| 5,397,323 A | 3/1995 | Taylor et al. |
| 5,417,210 A | 5/1995 | Funda et al. |
| 5,429,604 A | 7/1995 | Hammersmark et al. |
| 5,487,757 A | 1/1996 | Truckai et al. |
| 5,617,515 A | 4/1997 | MacLaren et al. |
| 5,624,380 A | 4/1997 | Takayama et al. |
| 5,752,112 A | 5/1998 | Paddock et al. |
| 5,755,713 A | 5/1998 | Bilof et al. |
| 5,759,151 A | 6/1998 | Sturges |
| 5,792,135 A | 8/1998 | Madhani et al. |
| 5,797,900 A | 8/1998 | Madhani et al. |
| 5,817,084 A | 10/1998 | Jensen |
| 5,855,569 A | 1/1999 | Komi |
| 5,868,760 A | 2/1999 | McGuckin, Jr. |
| 5,876,325 A | 3/1999 | Mizuno et al. |
| 5,892,860 A | 4/1999 | Maron et al. |
| 5,899,425 A | 5/1999 | Corey, Jr. |
| 5,982,791 A | 11/1999 | Sorin et al. |
| 6,030,130 A | 2/2000 | Paddock |
| 6,063,095 A | 5/2000 | Wang et al. |
| 6,066,090 A | 5/2000 | Yoon |
| 6,120,433 A | 9/2000 | Mizuno et al. |
| 6,132,368 A | 10/2000 | Cooper |
| 6,171,277 B1 | 1/2001 | Ponzi |
| 6,191,414 B1 | 2/2001 | Ogle et al. |
| 6,246,200 B1 | 6/2001 | Blumenkranz et al. |
| 6,275,628 B1 | 8/2001 | Jones et al. |
| 6,331,181 B1 | 12/2001 | Tierney et al. |
| 6,332,089 B1 | 12/2001 | Acker et al. |
| 6,347,892 B1 | 2/2002 | Paddock et al. |
| 6,352,503 B1 | 3/2002 | Matsui et al. |
| 6,366,722 B1 | 4/2002 | Murphy et al. |
| 6,371,952 B1 | 4/2002 | Madhani et al. |
| 6,389,187 B1 | 5/2002 | Greenaway et al. |
| 6,396,574 B1 | 5/2002 | Lee et al. |
| 6,441,577 B2 | 8/2002 | Blumenkranz et al. |
| 6,451,027 B1 | 9/2002 | Cooper et al. |
| 6,470,205 B2 | 10/2002 | Bosselmann et al. |
| 6,471,710 B1 | 10/2002 | Bucholtz |
| 6,478,028 B1 | 11/2002 | Paolitto et al. |
| 6,487,352 B1 | 11/2002 | Sobiski et al. |
| 6,554,793 B1 | 4/2003 | Pauker et al. |
| 6,569,084 B1 | 5/2003 | Mizuno et al. |
| 6,571,639 B1 | 6/2003 | May et al. |
| 6,572,629 B2 | 6/2003 | Kalloo et al. |
| 6,574,355 B2 | 6/2003 | Green |
| 6,575,644 B2 | 6/2003 | Paddock et al. |
| 6,578,967 B1 | 6/2003 | Paddock et al. |
| 6,645,196 B1 | 11/2003 | Nixon et al. |
| 6,648,816 B2 | 11/2003 | Irion et al. |
| 6,671,055 B1 | 12/2003 | Wavering et al. |
| 6,671,581 B2 | 12/2003 | Niemeyer et al. |
| 6,743,239 B1 | 6/2004 | Kuehn et al. |
| 6,758,843 B2 | 7/2004 | Jensen |
| 6,783,491 B2 | 8/2004 | Saadat et al. |
| 6,790,173 B2 | 9/2004 | Saadat et al. |
| 6,817,974 B2 | 11/2004 | Cooper et al. |
| 6,837,847 B2 | 1/2005 | Ewers et al. |
| 6,866,671 B2 | 3/2005 | Tierney et al. |
| 6,902,560 B1 | 6/2005 | Morley et al. |
| 6,936,042 B2 | 8/2005 | Wallace et al. |
| 6,942,613 B2 | 9/2005 | Ewers et al. |
| 6,960,162 B2 | 11/2005 | Saadat et al. |
| 6,960,163 B2 | 11/2005 | Ewers et al. |
| 6,984,203 B2 | 1/2006 | Tartaglia et al. |
| 6,991,602 B2 | 1/2006 | Nakazawa et al. |
| 6,994,703 B2 | 2/2006 | Wang et al. |
| 6,997,870 B2 | 2/2006 | Couvillon, Jr. |
| 7,041,052 B2 | 5/2006 | Saadat et al. |
| 7,042,573 B2 | 5/2006 | Froggatt |
| 7,090,637 B2 | 8/2006 | Danitz et al. |
| 7,090,683 B2 | 8/2006 | Brock et al. |
| 7,128,708 B2 | 10/2006 | Saadat et al. |
| 7,252,660 B2 | 8/2007 | Kunz |
| 7,320,700 B2 | 1/2008 | Cooper et al. |
| 7,371,028 B2 | 5/2008 | Gordon et al. |
| 7,594,912 B2 | 9/2009 | Cooper et al. |
| 7,725,214 B2 | 5/2010 | Diolaiti |
| 7,930,065 B2 | 4/2011 | Larkin et al. |
| 8,075,498 B2 | 12/2011 | Leo et al. |
| 8,281,670 B2 | 10/2012 | Larkin et al. |
| 8,784,435 B2 | 7/2014 | Cooper et al. |
| 9,039,685 B2 | 5/2015 | Larkin et al. |
| 9,060,678 B2 | 6/2015 | Larkin et al. |
| 9,060,793 B2 | 6/2015 | Larkin et al. |
| 9,066,739 B2 | 6/2015 | Larkin et al. |
| 9,084,624 B2 | 7/2015 | Larkin et al. |
| 9,101,380 B2 | 8/2015 | Larkin et al. |
| 9,125,679 B2 | 9/2015 | Larkin et al. |
| 9,241,769 B2 | 1/2016 | Larkin et al. |
| 9,526,583 B2 | 12/2016 | Larkin et al. |
| 2001/0049509 A1 | 12/2001 | Sekine et al. |
| 2001/0055462 A1 | 12/2001 | Seibel |
| 2002/0007110 A1 | 1/2002 | Irion |
| 2002/0055795 A1 | 5/2002 | Niemeyer et al. |
| 2002/0087169 A1 | 7/2002 | Brock et al. |
| 2002/0099293 A1 | 7/2002 | Fontenot et al. |
| 2002/0120252 A1 | 8/2002 | Brock et al. |
| 2002/0143319 A1 | 10/2002 | Brock |
| 2002/0173786 A1 | 11/2002 | Kortenbach et al. |
| 2003/0050649 A1 | 3/2003 | Brock et al. |
| 2003/0167061 A1 | 9/2003 | Schlegel et al. |
| 2003/0228039 A1 | 12/2003 | Green |

(56) References Cited

U.S. PATENT DOCUMENTS

| | | |
|---|---|---|
| 2003/0236505 A1 | 12/2003 | Bonadio et al. |
| 2004/0054355 A1 | 3/2004 | Gerbi et al. |
| 2004/0083808 A1 | 5/2004 | Rambow et al. |
| 2004/0138525 A1 | 7/2004 | Saadat et al. |
| 2004/0138529 A1 | 7/2004 | Wiltshire et al. |
| 2004/0153191 A1 | 8/2004 | Grimm et al. |
| 2004/0193146 A1* | 9/2004 | Lee ................... A61B 17/062 606/1 |
| 2004/0202400 A1 | 10/2004 | Kochergin et al. |
| 2005/0004431 A1 | 1/2005 | Kogasaka et al. |
| 2005/0043718 A1 | 2/2005 | Madhani et al. |
| 2005/0059960 A1 | 3/2005 | Simaan et al. |
| 2005/0065397 A1 | 3/2005 | Saadat et al. |
| 2005/0065398 A1 | 3/2005 | Adams |
| 2005/0075536 A1 | 4/2005 | Otsuka et al. |
| 2005/0096502 A1 | 5/2005 | Khalili |
| 2005/0102062 A1 | 5/2005 | Green |
| 2005/0107663 A1 | 5/2005 | Saadat et al. |
| 2005/0131343 A1 | 6/2005 | Abrams et al. |
| 2005/0215983 A1 | 9/2005 | Brock |
| 2005/0222554 A1 | 10/2005 | Wallace et al. |
| 2005/0251176 A1 | 11/2005 | Swanstrom et al. |
| 2005/0272977 A1 | 12/2005 | Saadat et al. |
| 2005/0284221 A1 | 12/2005 | Danisch et al. |
| 2006/0013523 A1 | 1/2006 | Childers et al. |
| 2006/0025652 A1 | 2/2006 | Vargas |
| 2006/0149418 A1 | 7/2006 | Anvari |
| 2006/0161136 A1 | 7/2006 | Anderson et al. |
| 2006/0200049 A1 | 9/2006 | Leo et al. |
| 2007/0021738 A1 | 1/2007 | Hasser et al. |
| 2007/0043338 A1 | 2/2007 | Moll et al. |
| 2007/0055291 A1 | 3/2007 | Birkmeyer et al. |
| 2007/0065077 A1 | 3/2007 | Childers et al. |
| 2007/0089557 A1 | 4/2007 | Solomon et al. |
| 2007/0135803 A1 | 6/2007 | Belson |
| 2007/0137371 A1 | 6/2007 | Devengenzo et al. |
| 2007/0151391 A1 | 7/2007 | Larkin et al. |
| 2007/0156020 A1 | 7/2007 | Foley et al. |
| 2007/0197896 A1 | 8/2007 | Moll et al. |
| 2007/0225554 A1 | 9/2007 | Maseda et al. |
| 2007/0265503 A1 | 11/2007 | Schlesinger et al. |
| 2007/0283970 A1 | 12/2007 | Mohr et al. |
| 2007/0287884 A1 | 12/2007 | Schena |
| 2007/0287889 A1 | 12/2007 | Mohr |
| 2007/0287992 A1 | 12/2007 | Diolaiti et al. |
| 2008/0058861 A1 | 3/2008 | Cooper et al. |
| 2008/0064921 A1 | 3/2008 | Larkin et al. |
| 2008/0064927 A1 | 3/2008 | Larkin et al. |
| 2008/0064931 A1 | 3/2008 | Schena et al. |
| 2008/0065097 A1 | 3/2008 | Duval et al. |
| 2008/0065098 A1 | 3/2008 | Larkin |
| 2008/0065099 A1 | 3/2008 | Cooper et al. |
| 2008/0065100 A1 | 3/2008 | Larkin |
| 2008/0065101 A1 | 3/2008 | Larkin |
| 2008/0065102 A1 | 3/2008 | Cooper |
| 2008/0065103 A1 | 3/2008 | Cooper et al. |
| 2008/0065104 A1 | 3/2008 | Larkin et al. |
| 2008/0065106 A1 | 3/2008 | Larkin |
| 2008/0065107 A1 | 3/2008 | Larkin et al. |
| 2008/0065109 A1 | 3/2008 | Larkin |
| 2008/0065110 A1 | 3/2008 | Duval et al. |
| 2008/0071288 A1 | 3/2008 | Larkin et al. |
| 2008/0071289 A1 | 3/2008 | Cooper et al. |
| 2008/0071290 A1 | 3/2008 | Larkin et al. |
| 2008/0071291 A1 | 3/2008 | Duval et al. |
| 2008/0091170 A1 | 4/2008 | Vargas et al. |
| 2008/0147089 A1 | 6/2008 | Loh et al. |
| 2008/0151041 A1 | 6/2008 | Shafer et al. |
| 2008/0156971 A1 | 7/2008 | Ogisu et al. |
| 2008/0212082 A1 | 9/2008 | Froggatt et al. |
| 2008/0287963 A1 | 11/2008 | Rogers et al. |
| 2009/0192524 A1 | 7/2009 | Itkowitz et al. |
| 2009/0248040 A1 | 10/2009 | Cooper et al. |
| 2009/0314131 A1 | 12/2009 | Bailey |
| 2009/0322001 A1 | 12/2009 | Luke et al. |
| 2009/0326322 A1 | 12/2009 | Diolaiti |
| 2009/0326552 A1 | 12/2009 | Diolaiti |
| 2009/0326553 A1 | 12/2009 | Mustufa et al. |
| 2010/0170519 A1 | 7/2010 | Romo et al. |
| 2010/0274087 A1 | 10/2010 | Diolaiti et al. |
| 2010/0332033 A1 | 12/2010 | Diolaiti et al. |
| 2011/0040305 A1 | 2/2011 | Gomez et al. |
| 2011/0040404 A1 | 2/2011 | Diolaiti et al. |
| 2011/0082365 A1 | 4/2011 | McGrogan et al. |
| 2011/0152879 A1 | 6/2011 | Williams |
| 2011/0184241 A1 | 7/2011 | Zubiate et al. |
| 2011/0196419 A1 | 8/2011 | Cooper |
| 2011/0201883 A1 | 8/2011 | Cooper et al. |
| 2011/0202068 A1 | 8/2011 | Diolaiti et al. |
| 2011/0224685 A1 | 9/2011 | Larkin et al. |
| 2011/0224688 A1 | 9/2011 | Larkin et al. |
| 2011/0277576 A1 | 11/2011 | Cooper |
| 2011/0277579 A1 | 11/2011 | Anderson et al. |
| 2011/0277580 A1 | 11/2011 | Cooper et al. |
| 2011/0277775 A1 | 11/2011 | Holop et al. |
| 2011/0277776 A1 | 11/2011 | McGrogan et al. |
| 2011/0282356 A1 | 11/2011 | Solomon et al. |
| 2011/0282357 A1 | 11/2011 | Rogers et al. |
| 2011/0282358 A1 | 11/2011 | Gomez et al. |
| 2011/0282359 A1 | 11/2011 | Duval |
| 2012/0010628 A1 | 1/2012 | Cooper et al. |
| 2014/0296872 A1 | 10/2014 | Cooper et al. |
| 2015/0245881 A1 | 9/2015 | Larkin et al. |
| 2015/0250546 A1 | 9/2015 | Larkin et al. |

FOREIGN PATENT DOCUMENTS

| | | |
|---|---|---|
| EP | 0776738 A2 | 6/1997 |
| EP | 1334700 A1 | 8/2003 |
| JP | S57190549 A | 11/1982 |
| JP | H06285009 A | 10/1994 |
| JP | H07504363 A | 5/1995 |
| JP | 2000093522 A | 4/2000 |
| JP | 2000166936 A | 6/2000 |
| JP | 2003275223 A | 9/2003 |
| WO | WO-9313916 A1 | 7/1993 |
| WO | WO-9729690 A1 | 8/1997 |
| WO | WO-0051486 A1 | 9/2000 |
| WO | WO-2004052171 A2 | 6/2004 |
| WO | WO-2005087128 A1 | 9/2005 |
| WO | WO-2005115226 A2 | 12/2005 |
| WO | WO-2006039092 A2 | 4/2006 |
| WO | WO-2007120329 A2 | 10/2007 |
| WO | WO-2007146987 A2 | 12/2007 |
| WO | WO-2008028149 A2 | 3/2008 |
| WO | WO-2009002701 A2 | 12/2008 |

OTHER PUBLICATIONS

Anisfield, Nancy; "Ascension Technology Puts Spotlight on DC Field Magnetic Motion Tracking," HP Chronicle, Aug. 2000, vol. 17, No. 9, 3 Pages.

Ascari, Luca et al., "A New Active Microendoscope for Exploring the Sub-Arachnoid Space in the Spinal Cord," Proc. IEEE International Conference on Robotics and Automation, 2003, pp. 2657-2662, vol. 2, IEEE.

Barnes Industries, Inc., "How a Ball Screw Works," 4 pages, Copyright 2007; Internet: http://www.barnesballscrew.com/ball.htm.

Berthold III, John W., "Historical Review of Microbend Fiber-Optic Sensors," Journal of Lightwave Technology, vol. 13, No. 7, Jul. 1995, pp. 1193-1199.

Blue Road Research, "Overview of Fiber Optic Sensors," 40 pages, first posted Dec. 8, 2004. Internet <www.bluerr.com/papers/Overview_of_FOS2.pdf>.

Cao, Caroline G.L., "Designing Spatial Orientation in Endoscopic Environments," Proceedings of the Human Factors and Ergonomics Society 45th Annual Meeting, 2001, pp. 1259-1263.

Cao, Caroline G.L., "Disorientation in Minimal Access Surgery: A Case Study," Proceedings of the IEA 2000/HFES 2000 Congress, pp. 4-169-4-172.

(56) References Cited

OTHER PUBLICATIONS

Childers, Brooks A., et al., "Use of 3000 Bragg grating strain sensors distributed on four eight-meter optical fibers during static load tests of a composite structure," SPIE 8th International Symposium on Smart Structures and Materials, Mar. 4-8, 2001, Newport Beach, California, 10 Pages.
Choi, Dong-Geol et al., "Design of a Spring Backbone Micro Endoscope," Conference on Intelligent Robots and Systems, 2007, pp. 1815-1821.
U.S. Appl. No. 11/762,185, filed Jun. 13, 2007.
U.S. Appl. No. 60/813,028, filed Jun. 13, 2006.
U.S. Appl. No. 60/813,029, filed Jun. 13, 2006.
U.S. Appl. No. 60/813,030, filed Jun. 13, 2006.
U.S. Appl. No. 60/813,075, filed Jun. 13, 2006.
U.S. Appl. No. 60/813,125, filed Jun. 13, 2006.
U.S. Appl. No. 60/813,126, filed Jun. 13, 2006.
U.S. Appl. No. 60/813,129, filed Jun. 13, 2006.
U.S. Appl. No. 60/813,131, filed Jun. 13, 2006.
U.S. Appl. No. 60/813,172, filed Jun. 13, 2006.
U.S. Appl. No. 60/813,173, filed Jun. 13, 2006.
U.S. Appl. No. 60/813,198, filed Jun. 13, 2006.
U.S. Appl. No. 60/813,207, filed Jun. 13, 2006.
U.S. Appl. No. 60/813,328, filed Jun. 13, 2006.
U.S. Appl. No. 61/334,978, filed May 14, 2010.
Cowie, Barbara M., et al., "Distributive Tactile Sensing Using Fibre Bragg Grating Sensors for Biomedical Applications," 1st IEEE / RAS-EMBS International Conference on Biomedical Robotics and Biomechatronics (BioRob 2006), Feb. 2006, pp. 312-317.
Danisch, Lee et al., "Spatially continuous six degree of freedom position and orientation sensor," Sensor Review, 1999, vol. 19, Issue 2, pp. 106-112.
Dario, Paolo et al., "A Miniature Device for Medical Intracavitary Intervention," Micro Electro Mechanical Systems '91 Proc IEEE 'An Investigation of Micro Structures, Sensors, Actuators, Machines and Robots', 1991, pp. 171-175, IEEE.
Duncan, Roger, "Sensing Shape: Fiber-Bragg-grating sensor arrays monitor shape at a high resolution," 2005, pp. 18-21, SPIE.
Extended European Search Report for Application No. EP20070798487, dated Jan. 30, 2015, 8 pages.
Gagarina, T. et al., "Modeling and experimental analysis of a new bellow type actuators for active catheter end-effector," Proc. 10th IEEE International Workshop on Robot and Human Interactive Communication, 2001, pp. 612-617, IEEE.
Gander, M.J. et al., "Bend measurement using Bragg gratings in multicore fibre," Electronics Letter, Jan. 20, 2000, vol. 36, No. 2, 2 Pages.
Hill, Kenneth O., "Fiber Bragg grating technology fundamentals and overview," IEEE Journal of Lightwave Technology, vol. 15, Issue 8, Aug. 1997, pp. 1263-1276.
Ikuta, Koji et al., "Development of remote microsurgery robot and new surgical procedure for deep and narrow space," Proc. IEEE International Conference on Robotics & Automation, 2003, pp. 1103-1108, vol. 1, IEEE.
Ikuta, Koji et al., "Shape memory alloy servo actuator system with electric resistance feedback and application for active endoscope," Proc. IEEE International Conference on Robotics and Automation, 1988, pp. 427-430, vol. 1, IEEE.
International Search Report for application No. PCT/US07/71085, dated Sep. 17, 2008, 2 pages.

Jin, Long et al., "Two-dimensional bend sensing with a cantilever-mounted FBG [Fiber Bragg Grating]," Meas. Sci. Technol., 2006, pp. 168-172, vol. 17, Institute of Physics Publishing.
Kreger, Stephen et al., "Optical Frequency Domain Reflectometry for High Density Multiplexing of Multi-Axis Fiber Bragg Gratings," 16th International Conference on Optical Fiber Sensors (OFS-16), Oct. 2003, Nara, Japan, pp. 526-529.
Lertpiriyasuwat, Vatchara et al., "Extended Kalman Filtering Applied to a Two-Axis Robotic Arm with Flexible Links," International Journal of Robotics Research, 2000, vol. 19., No. 3, pp. 254-270.
Martinez, A. et al., "Vector Bending Sensors Based on Fibre Bragg Gratings Inscribed by Infrared Femtosecond Laser," Electronics Letters, 2005, pp. 472-474, vol. 41—Issue 8.
Measurand, "ShapeTape Overview," Measurand ShapeTape Advantage, pp. 1-3, first posted Nov. 3, 2004. Internet <www.measurand.com/products/ShapeTape_overview.html>.
Meltz, Gerald, "Overview of Fiber Grating-Based Sensors," Proceedings of SPIE Distributed Multiplexed Fiber Optic Sensors VI, Nov. 27, 1996, Eds. Kersey et al.,vol. 2838, pp. 2-22.
Office Action dated Jun. 17, 2014 for Japanese Application No. 20130179563 filed Aug. 30, 2013, 7 pages.
PCT/US07/71085 Written Opinion, dated Sep. 17, 2008, 5 pages.
PCT/US09/46446 International Search Report and Written Opinion of the International Searching Authority, dated Dec. 14, 2009, 21 pages.
PCT/US09/46446 Partial International Search Report and Invitation to Pay Additional Fees, dated Sep. 18, 2009, 9 pages.
PCT/US2011/035113 International Search Report and Written Opinion of the International Searching Authority, dated Aug. 4, 2011, 13 pages.
Stieber, Michael E. et al., "Vision-Based Sensing and Control for Space Robotics Applications," IEEE Transactions on Instrumentation and Measurement, Aug. 1999, vol. 48, No. 4, pp. 807-812.
Sturges, Robert H. et al., "A Flexible, Tendon-Controlled Device for Endoscopy," The International Journal of Robotics Research, 1993, pp. 121-131, vol. 12—Issue 2 , SAGE Publications.
Szewczyk, Jerome et al., "An active tubular polyarticulated microsystem for flexible endoscope," Lecture Notes in Control and Information Sciences, vol. 271, Experimental Robotics VII, 2000, pp. 179-188, Springer-Verlag.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Wang, Yi-Ping et al., "A novel long period fiber grating sensor measuring curvature and determining bend-direction simultaneously," IEEE Sensors Journal, 2005, pp. 839-843, vol. 5—Issue: 5, IEEE.
Webster, Robert J. III et al., "Toward Active Cannulas: Miniature Snake-Like Surgical Robots," 2006, 7 pages.
Wong, Allan C. L. et al., "Multiplexed fibre Fizeau interferometer and fibre Bragg grating sensor system for simultaneous measurement of quasi-static strain and temperature using discrete wavelet transform," Measurement Science and Technology, 2006, pp. 384-392, vol. 17—Issue 2, Institute of Physics Publishing.
Zhang, Lunwei et al., "FBG Sensor Devices for Spatial Shape Detection of Intelligent Colonoscope," IEEE International Conference on Robotics and Automation, Apr. 2004, New Orleans, Louisiana, pp. 835-840.

\* cited by examiner

ROBOTIC SURGERY SYSTEM INCLUDING POSITION SENSORS USING FIBER BRAGG GRATINGS

CROSS-REFERENCE TO RELATED APPLICATIONS

This application is a continuation of U.S. patent application Ser. No. 13/049,003, filed Mar. 16, 2011, which is a continuation of U.S. patent application Ser. No. 11/491,384, filed on Jul. 20, 2006 and issued as U.S. Pat. No. 7,930,065 which claims the benefit of priority from U.S. provisional patent application Ser. No. 60/755,157, filed on Dec. 30, 2005, entitled "Modular Force Sensor," the disclosures all of which are incorporated herein in their entirety.

BACKGROUND

In robotically-assisted or telerobotic surgery, the surgeon typically operates a control device to control the motion of surgical instruments at the surgical site from a location that may be remote from the patient (e.g., across the operating room, in a different room or a completely different building from the patient) or immediately adjacent to the patient. The controller usually includes one or more manually-operated input devices, such as joysticks, exoskeletal gloves or the like, which are coupled (directly or indirectly) to the surgical instruments with servo motors for articulating the instruments at the surgical site. The servo motors are typically part of an electromechanical device or surgical manipulator that supports and controls the surgical instruments that have been introduced directly into an open surgical site or through trocar sleeves into a body cavity, such as the patient's abdomen. During the operation, the surgical manipulator provides mechanical articulation and control of a variety of surgical instruments, such as tissue graspers, needle drivers, electrosurgical cautery probes, etc., that each perform various functions for the surgeon, e.g., holding or driving a needle, grasping a blood vessel, or dissecting, cauterizing or coagulating tissue. A surgeon may employ a large number of different surgical instruments/tools during a procedure.

Robotic manipulators, particularly small ones of the type used in minimally-invasive surgery, generally need to transmit actuation forces and sensor information some distance through the structure of the robotic device, because the mass and size of presently-available actuators (e.g., motors) and sensors (e.g., position encoders) are too large to permit them to be directly located where the force and sensing is needed. In a mechanical device of a type used in minimally-invasive surgery, it is desirable to provide (a) significant force and (b) positioning precision at the tip of a small structure. However, the motors and sensors used are typically too large and heavy to be placed inside the patient's body. In addition, safety concerns make transmission of electrical power to actuators or sensors located inside the patient's body problematic. Therefore, in these robotic applications, it is desirable to transmit the actuation forces for multiple degrees of freedom over significant distances, and the desire to minimize the size of incisions places a premium on the cross-sectional area used for the structure and the transmission of the actuation forces. In addition, it is desirable to keep the transmission mechanism for these forces as stiff and friction-free as possible, so that the proximally sensed position of the proximal actuator may be used as a fair representation of the distally positioned joint.

There are many means known to transmit force over a distance. Some examples include: cables in tension; rods or tubes in compression; torsion; and hydraulic or pneumatic pressure. None of these force transmission means are ideal for minimally-invasive surgery, and therefore there are practical limits to the precision with which a distally mounted structure member can be moved, and the force it can provide. For example, cables may stretch, thereby leading to errors in the distal structure position relative to the position of the proximal driving mechanism. Compliant cables may also have significant friction with the supporting structure. Friction is notoriously difficult to model, may behave in a time-varying way and is dependent upon any number of variables, including the position (and past history of the position) of any intermediate joints in the structure, and when combined with compliant actuation can lead to stick-slip behavior. These errors limit the utility of the robot, limit the number of degrees of freedom that can be controlled remotely through a small structure, limit the use of the robot's state to provide haptic feedback, and are particularly severe for a flexible surgical robot which must accurately control many degrees of freedom of actuation at the end of a long, flexible structure.

Feedback regarding the actual position of a structure is a commonly applied mechanism for compensating for these errors. If the position of the distal part is accurately measured with minimal delays, control algorithms can compensate for many of the deficiencies of the force transmission mechanisms. While there are limits to the compensation that can be done with feedback, those limits cannot even be approached without accurate, timely information about the positions of the distally-mounted parts. The main restriction on the applicability of feedback in these types of robotic arms is the lack of an effective means of determining the position of parts mounted at the distal end of the structure.

Two methods of determining the position of a structure are proprioception and exteroception. Proprioception refers to the internal sensing of the position of the structure and exteroception refers to the external sensing of the position.

A proprioceptive system may monitor the motors actuating the movement of each joint in a robotic structure. By monitoring the degree of movement of each motor, the expected movement of each corresponding joint can be estimated. For example, the da Vinci Surgical System by Intuitive Surgical, Inc., of Sunnyvale, Calif. utilizes motor sensors (e.g., encoders) for position feedback. The encoders are co-located with the actuators, which are positioned outside of the patient body and drive the structure's joints through a cable mechanism. However, this method allows the position control loop to compensate only for error sources that occur between the actuator and the encoder. Error sources distal to the encoder are not observed by the encoder and thus cannot be compensated. This arrangement does not provide for compensation of errors introduced by any structures or drivetrain mechanisms that are distal to the encoders. In order to estimate the position of distal joints, the cable mechanism is modeled as infinitely stiff, so the motor position is assumed to be a reliable indication of the actual joint position. If the drivetrain between the actuator and the joint is not sufficiently stiff or other errors exist between the joint and the encoder, there will be a difference between actual joint orientation and the expected orientation based on the motor position. These joints are often mounted serially, so that the relative orientation of each of the links in the structure must be known and transformed to determine the position of the distal end of the structure. As a result, errors in the sensing of the orientations of intermediate links may compound along the way.

In other cases, position sensors may be positioned directly at the joints. This arrangement may be effective for larger structures, such as the Canadarm2 used on the International Space Station, and industrial robots. In robotically-assisted surgical systems having many degrees of freedom near the distal end, joint encoders do not offer much benefit as they are too large to be placed where the most problematic joints are located, and the connections required to transmit their position data back to the controller compete for space with the force-transmitting apparatus inside the arm.

Tachometers and accelerometers have been used, typically to estimate the robot's configuration at successive time steps and for force-control applications. These systems also do not provide complete position data and therefore cannot be used to compensate for some types of errors described above.

In systems which utilize exteroception, externally observed position feedback may be used to determine the position of a robotic structure.

For example, GPS-based location (especially differential GPS) has been used in outdoor environments, but typically can only be applied to large structures due to the relatively poor spatial resolution.

Field-based sensing can be accomplished using either AC or DC magnetic fields. In this approach, a small sensing element is placed at the tip of the structure to be monitored, and a magnetic field generated externally. While these systems can achieve good accuracy under ideal conditions, the accuracy rapidly degrades when metallic objects are nearby (as is the case in most surgical applications), and an external apparatus is needed to generate the field. In addition, these sensors do not directly encode the positions of the joints or links in a structure unless a sensor is provided on each link. Therefore, different configurations of the structure which result in the same position of the sensor are not distinguishable, which limits the use of this type of data for feedback compensation as described above.

Another approach is to utilize a dedicated set of unloaded cables, attached to the movable member at the distal end and to an encoder or position measurement device at the proximal end. Although unloaded, these cables are still subject to the same bending at the intermediate joints as are the actuation devices, and to provide feedback for many degrees of freedom, many cables must be used, requiring a larger structure.

Methods have been used involving a combination of sensing of the external environment, locating landmarks, and using this information to simultaneously construct a map of the environment and localize the robot. However, these systems are only applicable to larger and slower-moving systems, such as mobile robotic platforms. In the surgical applications considered here, these methods may be undesirable because the landmarks (e.g. patient anatomy) are not well defined and may change position as a result of disease states or during the surgical manipulations.

Techniques known as visual-servoing have been proposed, in which a camera mounted on the end of the robot arm is used in combination with joint encoders to control the position of the robot end-effector with respect to a tracked object in the field of view of an imaging device. This approach suffers from the need to provide joint position feedback and identifiable landmarks in the viewed scene, which are also problematic in surgical applications.

These techniques suffer from various deficiencies when utilized in robotic surgical applications and do not provide the type of information desired for implementing closed-loop control of such robotic mechanisms and compensating for the deficiencies in the force-transmission means described above. In addition, these techniques may be complex and expensive to implement.

Accordingly, it would be desirable to provide systems and methods for determining the position of a surgical instrument at a surgical site on a patient. In particular, it would be desirable for these systems and methods to provide real-time position feedback to the control system for a robotic surgical instrument.

SUMMARY

In accordance with embodiments of the present invention, a surgical instrument is provided, comprising: at least one articulatable arm having a distal end, a proximal end, and at least one joint region disposed between the distal and proximal ends; an optical fiber bend sensor provided in the at least one joint region of the at least one articulatable arm; a detection system coupled to the optical fiber bend sensor, said detection system comprising a light source and a light detector for detecting light reflected by or transmitted through the optical fiber bend sensor to determine a position of at least one joint region of the at least one articulatable arm based on the detected light reflected by or transmitted through the optical fiber bend sensor; and a control system comprising a servo controller for effectuating movement of the arm.

In accordance with other embodiments of the present invention, a surgical instrument is provided, comprising: at least one elongate arm comprising a passively-bendable region and an actively-controlled bendable region including at least one joint region; a control system comprising a servo controller for effectuating movement of the at least one joint region; an optical fiber bend sensor provided in at least one of the passively-bendable region and the actively-controlled bendable region; and a detection system coupled to the optical fiber bend sensor, said detection system comprising a light source and a light detector for detecting light reflected by or transmitted through the optical fiber bend sensor.

Other features and aspects of the invention will become apparent from the following detailed description, taken in conjunction with the accompanying drawings which illustrate, by way of example, the features in accordance with embodiments of the invention. The summary is not intended to limit the scope of the invention, which is defined solely by the claims attached hereto.

DETAILED DESCRIPTION

Figure 1:
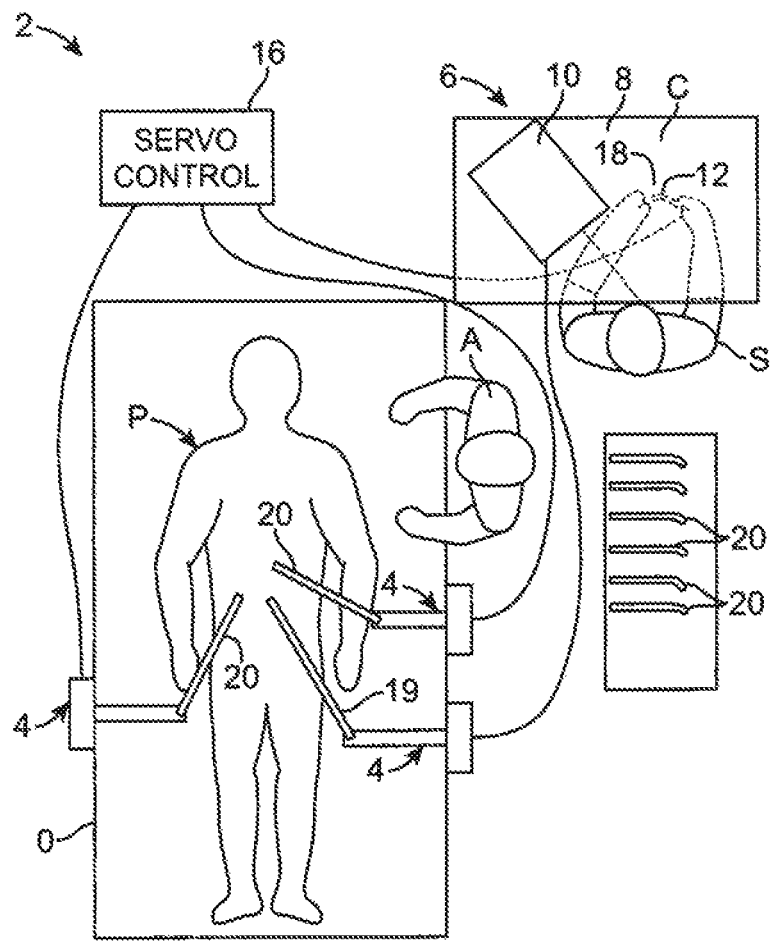
FIG. 1 shows a robotic surgical system, in accordance with embodiments of the present invention.

In the following description, reference is made to the accompanying drawings which illustrate several embodiments of the present invention. It is understood that other embodiments may be utilized and mechanical, compositional, structural, electrical, and operational changes may be made without departing from the spirit and scope of the present disclosure. The following detailed description is not to be taken in a limiting sense, and the scope of the embodiments of the present invention is defined only by the claims of the issued patent.

The terminology used herein is for the purpose of describing particular embodiments only and is not intended to be limiting of the invention. Spatially relative terms, such as "beneath", "below", "lower", "above", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

As used herein, the singular forms "a", "an" and "the" are intended to include the plural forms as well, unless the context indicates otherwise. It will be further understood that the terms "comprises" and/or "comprising" specify the presence of stated features, steps, operations, elements, and/or components, but do not preclude the presence or addition of one or more other features, steps, operations, elements, components, and/or groups thereof.

Described herein are embodiments of a multi-component system, apparatus, and method for performing robotically-assisted surgical procedures on a patient, particularly including open surgical procedures, neurosurgical procedures, such as stereotaxy, and endoscopic procedures, such as laparoscopy, arthroscopy, thoracoscopy and the like. The system and method of the present invention may be particularly useful as part of a robotic surgical system that allows the surgeon to manipulate the surgical instruments through a servo controller from a location remote from the patient. To that end, the manipulator apparatus of the present invention may be driven by a controller to form a telepresence system. The systems may comprise a master-slave configuration in which the controller and manipulator apparatus are separate devices, or may comprise an augmented system in which the controller and manipulator are provided as part of a single device. A description of a suitable slave-master system can be found in U.S. patent application Ser. No. 08/517,053, filed Aug. 21, 1995, the complete disclosure of which is incorporated herein by reference for all purposes.

Referring to FIG. 1, a robotic surgical system 2 is illustrated according to an embodiment of the present invention. A similar system is described in U.S. provisional patent application Ser. No. 60/755,157, filed on Dec. 30, 2005, entitled "Modular Force Sensor," the disclosure of which is incorporated herein in its entirety. As shown in FIG. 1, the robotic system 2 generally includes one or more surgical manipulator assemblies 4 mounted to or near an operating table O, and a control assembly 6 for allowing the surgeon S to view the surgical site and to control the manipulator assemblies 4. The system 2 will also include one or more viewing scope assemblies 19 and a plurality of surgical instruments 20 adapted to be removably coupled to manipulator assemblies 4 (discussed in detail below). In some cases, the scope assemblies 19 may be integral with the surgical instruments 20. The robotic system 2 may include one or more manipulator assemblies 4 and preferably three or four manipulator assemblies 4. The exact number of manipulator assemblies 4 will depend on the surgical procedure and the space constraints within the operating room among other factors. As discussed in detail below, one of the manipulator assemblies 4 may operate a viewing scope assembly 19 (e.g., in endoscopic procedures) for viewing the surgical site, while the other manipulator assemblies 4 operate surgical instruments 20 for performing various procedures on the patient P.

Control assembly 6 may be located at a surgeon's console C which is usually located in the same room as operating table O so that the surgeon may speak to his/her assistant(s) A and directly monitor the operating procedure. However, it should be understood that the surgeon S can be located in a different room or a completely different building from the patient P. Control assembly 6 generally includes a support 8, a monitor 10 for displaying an image of the surgical site to the surgeon S, and one or more control device(s) 12 for controlling the manipulator assemblies 4. The control device(s) 12 may include a variety of input devices, such as joysticks, gloves, trigger-guns, hand-operated controllers, voice recognition devices or the like. Preferably, the control device(s) 12 will be provided with the same degrees of freedom as the associated surgical instruments 20 to provide the surgeon with telepresence, or the perception that the control device(s) 12 are integral with the instruments 20 so that the surgeon has a strong sense of directly controlling instruments 20. In some embodiments, the control devices 12 are manual input devices which move with six degrees of freedom, and which may also include an actuatable handle for actuating instruments (for example, for closing grasping saws, applying an electrical potential to an electrode, or the like).

Position, applied force, and tactile feedback sensors (not shown) may also be employed on instrument assemblies 20 to transmit information regarding position, applied force, and tactile sensations from the surgical instrument back to the surgeon's hands as he/she operates the robotic system. One suitable system and method for providing telepresence to the operator is described in U.S. patent application Ser. No. 08/517,053, filed Aug. 21, 1995, which is incorporated by reference herein in its entirety.

Monitor 10 may be operatively coupled to the viewing scope assembly 19 such that an image of the surgical site is provided adjacent the surgeon's hands on surgeon console C. Preferably, monitor 10 will display on a display 18 an image of the surgical site and surgical instruments. The display 18 and the master control devices 12 may be oriented such that the relative positions of the imaging device in the scope assembly and the surgical instruments are similar to the relative positions of the surgeon's eyes and hands so the operator can manipulate the end effector and the hand control as if viewing the workspace in substantially true presence. By true presence, it is meant that the presentation of an image is a true perspective image simulating the viewpoint of an operator that is physically manipulating the surgical instruments 20.

As shown in FIG. 1, a servo controller 16 is provided for controlling the mechanical motion of the manipulator assemblies 4 in response to movement of the master control devices 12. In some embodiments, servo controller 16 may provide force and torque feedback from the surgical instruments 20 to the hand-operated control devices 12. To operate effectively with this system, manipulator assemblies 4 may be provided with a relatively low inertia, and the drive motors may have relatively low ratio gear or pulley couplings. Any suitable conventional or specialized servo controller may be used.

Servo controller 16 may be separate from, or integral with manipulator assemblies 4. In some embodiments, the servo controller 16 and manipulator assemblies 4 are provided as part of a robotic arm cart positioned adjacent to the patient's body. The servo controller 16 transmits signals instructing the manipulator assemblies 4 to move instruments having shafts which extend into an internal surgical site within the patient body via openings in the body. Robotic surgery systems and methods are further described in U.S. Pat. No. 5,797,900, filed on May 16, 1997, issued on Aug. 25, 1998, U.S. Pat. No. 6,132,368, filed on Nov. 21, 1997, issued on Oct. 17, 2000, U.S. Pat. No. 6,331,181, filed on Oct. 15, 1999, issued on Dec. 18, 2001, U.S. Pat. No. 6,441,577, filed on Apr. 3, 2001, issued on Aug. 27, 2002, U.S. Pat. No. 6,902,560, filed on Jan. 6, 2004, issued on Jun. 7, 2005, U.S. Pat. No. 6,936,042, filed on Apr. 16, 2002, issued on Aug. 30, 2005, and U.S. Pat. No. 6,994,703, filed on Dec. 4, 2002, issued on Feb. 7, 2006, the full disclosures of which are incorporated herein by reference. A suitable robotic surgical system currently in use is the da Vinci S Surgical System by Intuitive Surgical, Inc.

Each of the manipulator assemblies 4 may support a surgical instrument 20 and may comprise a series of manually articulatable linkages, generally referred to as set-up joints, and a robotic manipulator. The manipulator assemblies 4 enable the instrument 20 to be rotated around a point in space, as more fully described in issued U.S. Pat. Nos. 6,331,181, and 5,817,084, the full disclosures of which are incorporated herein by reference. The robotic manipulators may pivot the instrument about a pitch axis, a yaw axis, and an insertion axis (which is aligned along a shaft of the instrument). The instrument has still further driven degrees of freedom as supported by the manipulator, including sliding motion of the instrument along the insertion axis.

The robotic manipulator assemblies 4 may be driven by a series of actuators (e.g., motors). These motors actively move the robotic manipulators in response to commands from the servo control 16. The motors are further coupled to the surgical instrument so as to rotate the surgical instrument about the insertion axis, and to articulate a wrist at the distal end of the instrument about at least one, and often two or more, degrees of freedom. Additionally, the motors can be used to actuate an articulatable end effector of the instrument for grasping tissues in the jaws of a forceps or the like. The motors may be coupled to at least some of the joints of the surgical instrument using cables, as more fully described in U.S. Pat. Nos. 6,331,181, and 5,792,135, the full disclosures of which are also incorporated herein by reference. As described in those references, the manipulators will often include flexible members for transferring motion from the drive components to the surgical instrument. Each actuator may effectuate movement of one or more joint members in the instrument. For endoscopic procedures, the manipulators may include a cannula, which supports the surgical instrument, allowing the surgical instrument to rotate and move axially through the central bore of the cannula.

In accordance with embodiments of the present invention, a surgical instrument is provided. This surgical instrument includes an elongate body having a positionable distal end and at least one bendable region, such as a joint region or a flexible region. An optical fiber bend sensor comprising one or more optical fibers is provided in the bendable region of the body. Each of these optical fibers includes a Fiber Bragg Grating, preferably a collinear array of Fiber Bragg Gratings. A strain sensor system comprising a light source and a light detector is used to measure strain in the optical fibers in order to determine a position and shape of the body. This shape and position information can be used to assist in controlling movement of the robotic manipulator and/or surgical instrument. This position information may include both translational and rotational position.

Figure 2:
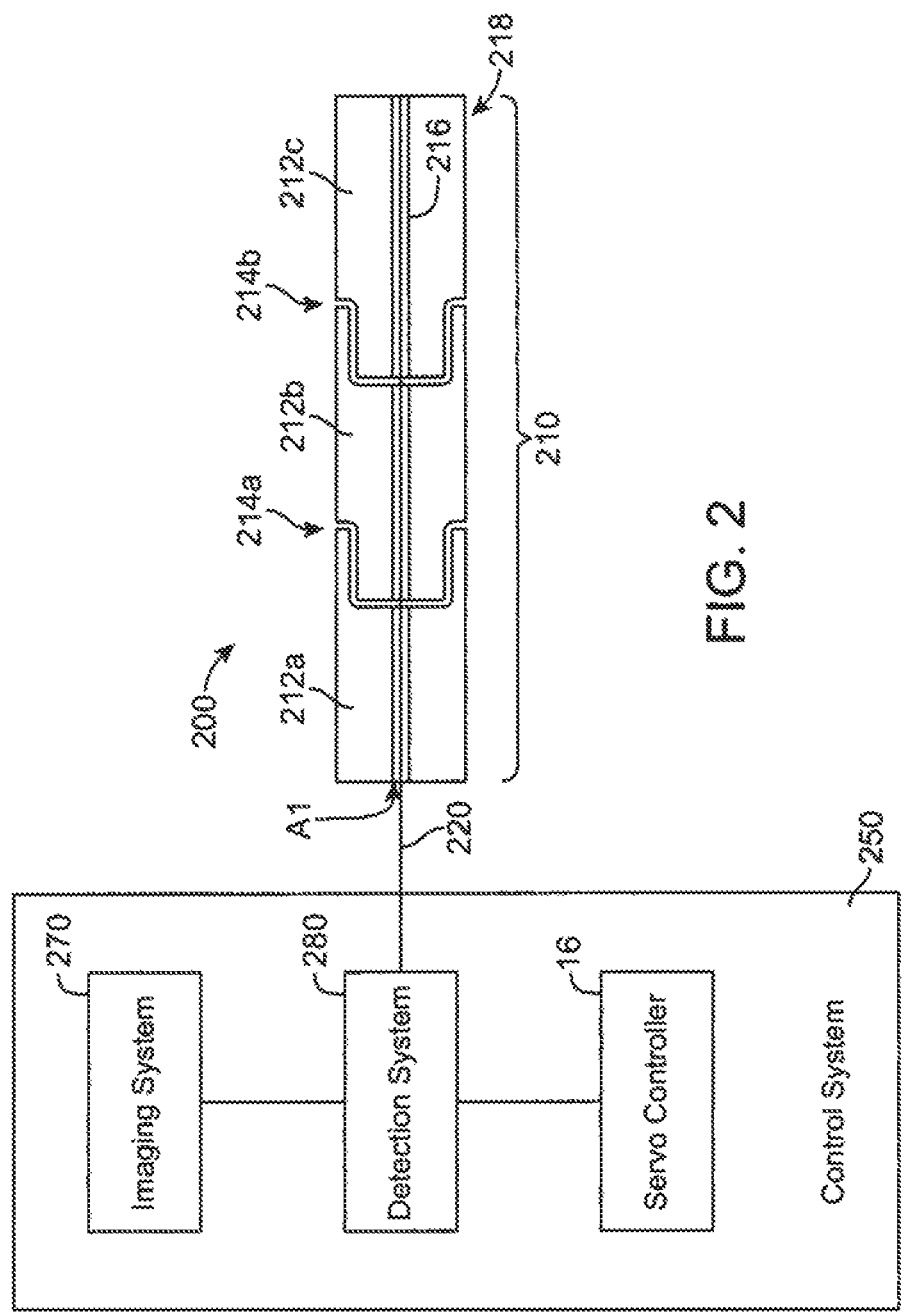
FIG. 2 shows a simplified block diagram of a surgical instrument, in accordance with embodiments of the present invention.

FIG. 2 shows a simplified block diagram of a surgical instrument 200, in accordance with embodiments of the present invention. The instrument 200 includes an elongate body 210 comprising a plurality of body segments 212 coupled to adjacent body segments 212 via joint regions 214. Each joint region 214 may provide, one, two, or more degrees of freedom for the instrument 200. A channel 216 passes through the elongate body 210, and an optical fiber 220 is provided within the channel 216. A sensor control system 250 is coupled to a proximal end of the optical fiber 220. In this embodiment, the body segments 212 are cylindrical in shape having a diameter of approximately 5 mm, and the fiber 220 has a diameter of approximately 200 um. In other embodiments, the shapes and dimensions of the components may vary.

Fiber optic bend sensors for determining a shape of a structure have been used. For example, optical fibers including Fiber Bragg Gratings (FBG) have been used in a variety of applications for providing strain measurements in structures in one or more dimensions. Various systems and methods for monitoring the shape and relative position of a optical fiber in three dimensions are described in U.S. patent application publication no. 2006/0013523, filed on Jul. 13, 2005, U.S. provisional patent application Ser. No. 60/588,336, filed on Jul. 16, 2004, and U.S. Pat. No. 6,389,187, filed on Jun. 17, 1998, the disclosures of which are incorporated herein in their entireties.

In accordance with embodiments of the present invention, an optical fiber, such as the optical fibers described in U.S. patent application publication no. 2006/0013523, is utilized as optical fiber 220 for monitoring the shape and relative position of each body segment 212 in the instrument 200. This information, in turn, in can be used to determine other related variables, such as velocity and acceleration of the parts of a surgical instrument. By obtaining accurate measurements of one or more of these variables in real time, the controller can improve the accuracy of the robotic surgical system and compensate for errors introduced in driving the component parts. The sensing may be limited only to the degrees of freedom that are actuated by the robotic system, or may be applied to both passive (e.g., unactuated bending of the rigid members between joints) and active (e.g., actuated movement of the instrument) degrees of freedom.

In this embodiment, the optical fiber 220 comprises three cores contained within a single cladding. Each core may be single-mode with sufficient distance and cladding separating the cores such that the light in each core does not interact significantly with the light carried in other cores. In other embodiments, the number of cores may vary or each core may be contained in a separate optical fiber.

An array of Fiber Bragg Gratings is provided within each core. Each Fiber Bragg Grating comprises a series of modulations of the core's refractive index so as to generate a spatial periodicity in the refraction index. The spacing may be chosen so that the partial reflections from each index change add coherently for a narrow band of wavelengths, and therefore reflect only this narrow band of wavelengths while passing through a much broader band. During fabrication of the Fiber Bragg Gratings, the modulations are spaced by a known distance, thereby causing reflection of a known band of wavelengths. However, when a strain is induced on the fiber core, the spacing of the modulations will change, depending on the amount of strain in the core.

To measure strain, light is sent down the fiber, and the reflected wavelength is a function of the strain on the fiber and its temperature. This FBG technology is commercially available from a variety of sources, such as Smart Fibres Ltd. of Bracknell, England. When applied to a multicore fiber, bending of the optical fiber induces strain on the cores that can be measured by monitoring the wavelength shifts in each core. By having two or more cores disposed off-axis in the fiber, bending of the fiber induces different strains on each of the cores. These strains are a function of the local degree of bending of the fiber. Regions of the cores containing FBGs, if located at points where the fiber is bent, can thereby be used to determine the amount of bending at those points. These data, combined with the known spacings of the FBG regions, can be used to reconstruct the shape of the fiber. Such a system has been described by Luna Innovations. Inc. of Blacksburg, Va.

A control system 250 is also provided for detecting the position of the surgical instrument 200 and for utilizing that information to assist in surgical procedures. In this embodiment, the control system 250 comprises a detection system 260 coupled to an imaging system 270 and the servo controller 16. The detection system 260 is utilized for generating and detecting the light used for determining the position of the instrument 200. The imaging system 270 is used to provide the surgeon or other operator with real-time position information for use in the control of the instrument 200. The servo controller 16 may utilize the position information as feedback for positioning the instrument 200.

Figure 3:
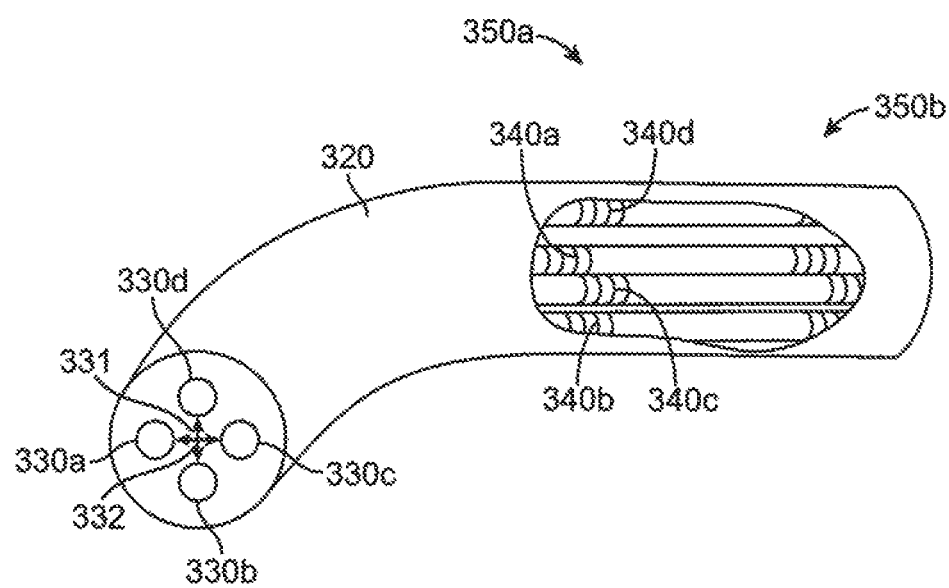
FIG. 3 is a simplified cross-sectional view of an exemplary optical fiber, which may be used in accordance with embodiments of the present invention.
Figure 4:
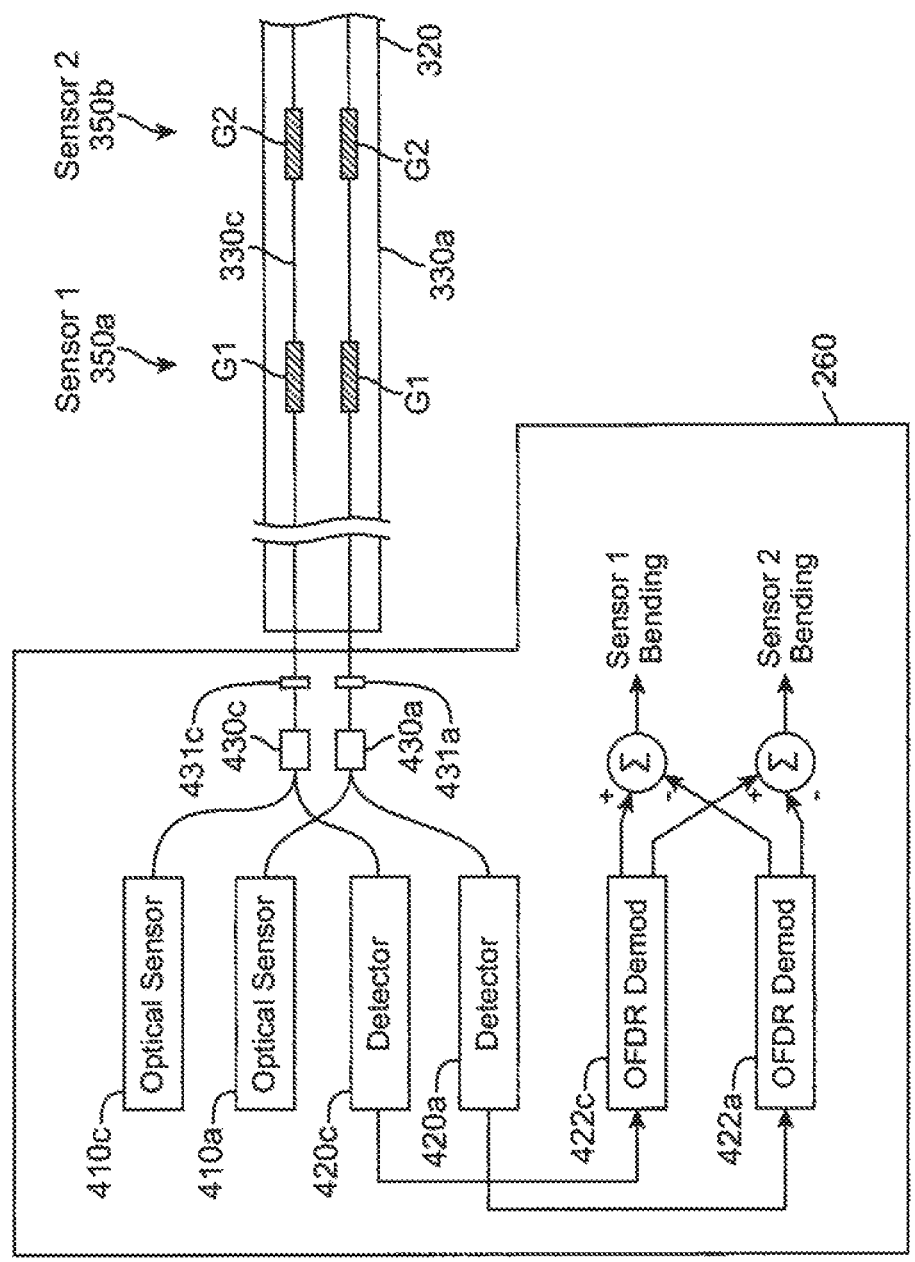
FIG. 4 is an exemplary block diagram of a first pair of opposing cores and the associated interrogation mechanisms.

FIG. 3 is a simplified cross-sectional view of an exemplary optical fiber 320, which may be used in accordance with embodiments of the present invention. In other embodiments, other types of fibers may be used, as would be understood by one of ordinary skill in the art. In this embodiment, the fiber 320 includes four optical cores 330a-330d disposed at equal distances from the axis of the fiber 320 such that in cross-section, opposing pairs of cores 330a-330d form orthogonal axes, first axis 331 and second axis 332. In each core 330a-330d, an array of collinear Fiber Bragg Gratings are disposed at known positions along the lengths of each core 330a-330d such that the Fiber Bragg Gratings 340a-340d for all four cores 330a-330d are aligned at a plurality of sensor regions 350a-350b. FIG. 4 is an exemplary block diagram of a first pair of opposing cores 330a, 330c and the associated interrogation mechanisms.

A bending of the fiber 320 in one of the sensor regions 350 will lengthen at least one core 330a-330d with respect to the opposing core 330a-330d. Interrogation of this length differential enables the angle and radius of bending to be extracted. This interrogation may be performed using the detection system 260, as described below.

There are a variety of ways of multiplexing the Fiber Bragg Gratings so that a single fiber core can carry many sensors and the readings of each sensor can be distinguished. In some embodiments, Optical Frequency Domain Reflectometry (OFDR) may be used in which the Fiber Bragg Gratings, all with the same grating period, are placed along each of the cores, and each core is terminated at the proximal end with a partially reflecting mirror. The Fiber Bragg Gratings are placed in such a way that the distance from each grating to the reflector is unique, which causes the reflection spectrum of each Fiber Bragg Grating to be modulated with a unique modulation frequency, thereby allowing the individual reflection spectra to be determined. In addition, OFDR may be used to interrogate the array of Fiber Bragg Gratings with sufficiently low delays such that that the bending data can be used as a feedback signal in a real-time motion control loop.

In the embodiment shown in FIG. 4, one OFDR FBG interrogation system is applied to each of the fiber cores. This interrogation system comprises an optical source 410 and an optical detector 420 operably coupled to each core 330 via a coupling device 430. A broadband reflector 431 is positioned at a location between the coupling device and the first sensor region 350a. The optical detectors 420 may comprise, e.g., PIN photodiodes for detecting signal reflected by the Fiber Bragg Gratings. The optical detectors 420, in turn, are coupled to OFDR demodulators 422 to determine the strain in sensor region 350 of each core 330 associated with the detected signal. The optical source 410 used in the OFDR interrogation system may be, e.g., a tunable laser, and provides high-coherence light that can be swept over a broad band of wavelengths. This light is coupled into each of the fiber cores, and the light reflected from the core is measured as the light source is swept in wavelength. The reflected light is a sum of the reflections from each of the Fiber Bragg Gratings along the core, but since each reflection is modulated with a distinct frequency (determined by the grating's distance from the broadband reflector), the reflection spectrum of each grating can be separated from the others using the data acquired in a single scan of the core. The shift in each grating is proportional to the strain in that core at the location of the grating, and the strain-induced shifts of the reflection spectrum of a pair of co-located gratings can be subtracted as shown in FIG. 4 to give a result proportional to the degree of bending applied to the multi-core fiber at the axial location of the grating pair.

For embodiments which detect position based on two degrees of freedom at each joint of the surgical instrument, at least three fiber cores 330 are utilized, with an interrogation system for each fiber core 330. In the embodiment illustrated in FIG. 3, four cores 330 are utilized, but in FIG. 4, only a first pair of opposing cores 330a, 330c is shown. It will be understood that a similar interrogation system arrangement will be provided for the second pair of opposing cores 330b, 330d. For a system in which three cores are used, there are three raw data sets generated by the three detectors, and three OFDR calculations, each OFDR calculation providing an output for each FBG region along the core.

As a result, the differences in strain between the Fiber Bragg Gratings G1, G2 in the first pair of opposing cores 330a, 330c and the second pair of opposing cores 330b, 330d in each sensor region 350 can be used to determine the fiber's bending at each instrumented axial location corresponding to the sensor region 350. With four cores 330a-330d disposed equally around the fiber's neutral axis, the strains measured for each pair of opposing cores 330 are subtracted. The difference between strains of the opposing cores 330a and 330c is proportional to the degree of bending along the first axis 331, and the difference between strains of the opposing cores 330b and 330d is proportional to the degree of bending along the second axis 332.

In the embodiment shown in FIG. 2, the instrument 200 comprises rigid body segments 212 coupled together by discrete joint regions 214. In this case, because the bending of the instrument 200 will occur at the joint regions 214, it is most desirable to position each sensor region 350 so that the curvature of the fiber 220 at the joint region 214 maintains a fixed axial relation to the joint angle over the entire range of joint motion. This may be accomplished by forming the channel 216 along the neutral axis of the instrument 200, so that there is no axial displacement of the fiber 220 as the joints are moved. As a result, it will be easier to correlate the detected strains with bending in particular joint regions 214.

In other embodiments, it may not be desirable or practical to position the fiber 220 on the neutral axis of the instrument 200. If the fiber 220 is positioned off-axis, then bending of the instrument 200 will change the length of the path of the fiber 220 through the channel 216 in the instrument 200. If the extent of bending is very small, then the fiber 220 may stretch or compress to accommodate the change in path length. Thus, the fiber 220 may have multiple fixed connection points with the instrument 200. This arrangement may be undesirable in some cases because increased axial loading of the fiber increases the common-mode signal in the fiber cores, thereby reducing the accuracy of the bending measurement. Considering a single pair of cores on opposite sides of the fiber's neutral axis, if there is no overall strain on the fiber, then bending at the sensor causes one FBG wavelength to shift down and the other to shift up by the same amount, thereby resulting in a zero common-mode signal. If, however, there is an overall strain on the fiber, both FBG wavelengths will shift in the same direction, in the absence of any bending at the sensor. Because each core is only a small distance (e.g., ~75 μm) from the fiber's neutral axis, the strains on the individual cores caused by bending of the fiber are quite small. Therefore, even a small axial strain on the fiber introduces a large common-mode signal, and gain errors between the two sensor paths may result in a false differential reading caused by the large common-mode signal, falsely indicating bending when the fiber is, in fact, straight.

If the extent of bending is large, then the change in path length can be greater than can be accommodated by the elasticity of the fiber 220. Thus, it may be desirable to have the fiber 220 translate axially relative to the instrument 200, causing the sensor regions 350 to also translate axially relative to the joint regions 214. One way to allow for this translation is to ensure that the length of each sensor region (e.g. 350a) exceeds the length of its associated joint region (e.g. 214a) by a sufficient amount, and that the joint regions are spaced sufficiently apart by rigid body segments 212, so that no matter how the joints are bent, the cumulative translation is not enough to shift the associated sensor region 350 away from the joint region, and also not enough to cause one sensor region to shift into the area of a neighboring joint region. Thus a one-to-one correspondence between joint regions and associated sensor regions is always maintained. This design will cause only a portion of the FBG to expand or contract with the joint bending, and thus the associated FBG reflectance spectrum will change shape with bending, rather than shifting up or down as they would if the entire FBG experienced the strain of bending.

Alternately, the known mechanical properties of the fiber 220 and the constraints on the shape of the fiber 220 when the instrument 200 is bent in various positions can be used to model the shifts in the Fiber Bragg Grating sensor readings. The joint positions can then be derived based on this model. This derivation can be accomplished by analyzing the shape of the reflection spectrum, which will change if a portion of the fiber in the FBG region is bent, but not the entire FBG region. Based on the observable effects on the reflection spectrum caused by bending confined to only a portion of the FBG region, and a forward model of joint angle to reflection spectrum can be derived. This forward model can then be inverted to obtain the joint angle estimate from the measured reflection spectrum.

In the simplified example shown in FIG. 2, the instrument 200 includes three rigid body segments 212 coupled by two joint regions 214, with the first body segment 212a coupled to the second body segment 212b via the first joint region 214a, and the second body segment 212b coupled to the third body segment 212c via the second joint region 214b. In one embodiment, the proximal end of the fiber 220 may be attached to the channel 216 of the instrument 200 at point A1, thereby fixing axial position of the fiber 220 relative to the instrument 200 at point A1. The distal end of the fiber 220 may be left free to slide axially relative to the channel 216. If the channel 216 is not provided on the neutral axis of the instrument 200, then when the instrument 200 is bent at the first joint region 214a, the fiber 220 may slide forward or backward through the channel 216, depending on the direction of rotation relative to the location of the channel 216. As a result, the sensor region 350 associated with the second joint region 214b will translate relative to the joint region 214b.

Compensation for the movement of the sensor region 350 may be accomplished in a variety of ways. For example, the detection of the strain in the first sensor region 350 associated with the first joint region 214a can be used to determine the direction and extent of rotation of the first joint region 214a. Based on this information, the expected location of the second sensor region 350 relative to the second joint region 214b can be determined. This determination can be accomplished by calculating the axial displacement based on predetermined models, or by looking up the axial displacement in a pre-calibrated table.

This information, in turn, is used in conjunction with the detected signals reflected from the second sensor region 350 to determine the direction and extent of rotation of the second joint region 214b. The information regarding the axial shifting of the second sensor region 350 may be used to compensate for the change in reflected signal caused by the shifting. Based on the known position and orientation of the first body segment 212a, the calculated direction and extent of rotation of the first and second joint regions 214, and the known length of the third body segment 212c, the position of the distal end 218 of the instrument may then be determined. In embodiments having a greater number of body segments, a similar determination may be made for each body segment based on the information received from the preceding body segments.

A similar situation occurs when the bending of a joint region 214 is acute enough that the length of the bent region does not extend over the entirety of the sensor region 350, even though no significant axial translation of the fiber 220 relative to the joint region 214 occurs. Because the strained portion of the sensor region 350 does not encompass the entire length of the sensor region 350, a change in spectral shape, rather than a simple shift of the reflectance spectrum, will occur.

Alternately, the sensor regions 350 may be made short enough that axial translation of the fiber 220 will move them partially out of the joint regions 214. As with the case described above, the result of this bending applied to only part of the sensor regions 350 is that the shape of the FBG reflectance spectrum will shift, rather than a simple shift in the center wavelength of the spectrum. In this case, the known axial shift in the fiber 220 at each joint region 214 can be used to assist in determining the degree of bending of the fiber 220 at each successive joint region 214. If, for example, the fiber 220 is anchored at the proximal end of the structure, the axial position of the fiber 220 at the first joint region 214 is fixed, and therefore the effects of the bending of the first joint region 214 on the FBG reflectance spectrum (a shift in the spectrum, a shape change, or a combination of the two), is known, and a measurement of the reflectance spectrum shape and shift can be directly used to determine the bend angle of this first joint region 214. That bend angle, along with the known structure of the channel containing the sensor fiber 220, can be used to determine the degree of axial shift in the fiber 220 at the second joint region 214. Therefore, the effects of the bending of the second joint region 214 on the FBG reflectance spectrum of its associated sensor region 350 become known, and the measurement of that reflectance spectrum can be used to determine the bend angle of the second joint region 214. This procedure can be iterated for each joint region 214 in the structure serially.

Figure 10:
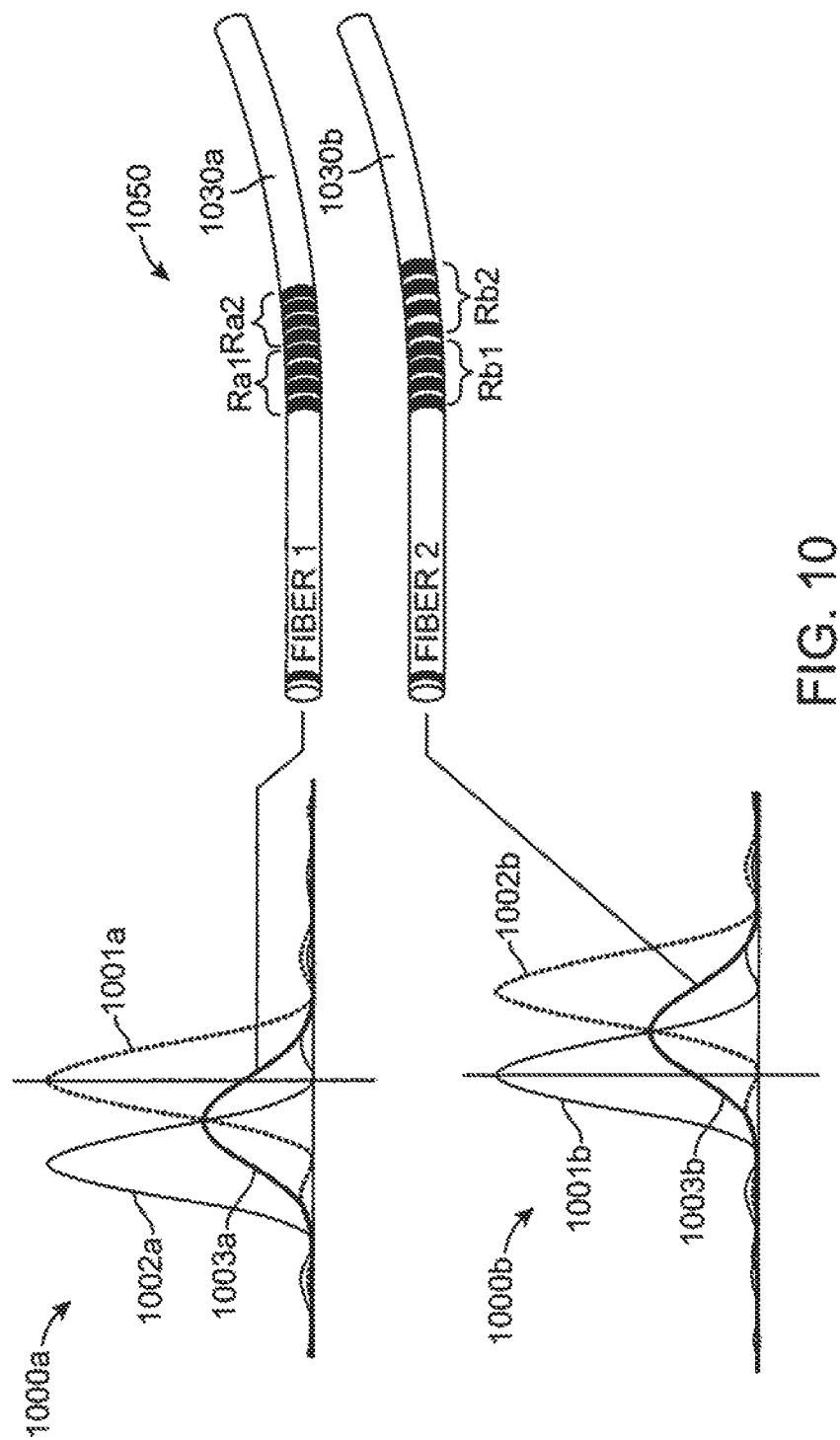
FIG. 10 illustrates a possible spectrum that may result when only part of a sensor region is contained within a joint region.

FIG. 10 illustrates a possible spectrum that may result when only part of a sensor region is contained with a joint region. This situation may arise when the fiber shifts axially, thereby moving part of the sensor region outside the joint region. Alternatively, this situation may arise if the sensor region is made long enough so that the entire joint region is covered by the FBG, but only a portion of the FBG is strained by the joint motion. As shown in FIG. 10, a sensor region 1050 comprising a pair of fiber cores 1030a-1030b is positioned so that approximately half of the sensor region 1050 is inside of the joint region. Therefore, in both fiber cores 1030a-1030b, a first portion Ra1, Rb1 that is outside of the joint region is unstressed, and a second portion Ra2, Rb2 which is inside of the joint region is under stress when the joint region is bent. In this case, Ra2 is compressed and Rb2 is extended.

Each of the plots 1000a-1000b shows the reflectance spectrum of the single Fiber Bragg Grating section in each core 1030a-1030b, respectively. The vertical axis corresponds to the intensity of the reflection, and the horizontal access corresponds to wavelength (with wavelength increasing from left to right). The first line 1001a-1001b corresponds to the reflectance spectrum intensity when the fiber is unbent, and therefore each Fiber Bragg Grating is at its nominal wavelength. The second line 1002a-1002b corresponds to the reflectance spectrum that would result if the entire length of the Fiber Bragg Grating region were bent. The third line 1003a-1003b shows the reflectance spectrum corresponding to the partial bending illustrated in FIG. 10.

For fiber core 1030a, which is partially compressed by the bending, the reflectance spectrum of the bent section shifts to shorter wavelengths, but the partial reflections from this strained section Ra2 combine linearly with the partial reflections from the unstrained section Ra1. These reflections add coherently to produce the total reflection 1003a. Because part of the reflected light is shifted and part is not, the reflectance spectrum 1003a changes in both shape and center point position from the default spectrum 1001a. For the illustrated case, where the shift in the bent section is roughly equal to the spectral width of the reflection from the entire grating, the net result is a broadening of the spectrum, as illustrated by the third line 1003a. For more extreme shifts, the spectrum may split into two distinct peaks, and because the reflections add coherently and the detection system measures the intensity of the reflected light, the intensity of each peak will be one quarter of that of the unbent grating (where the grating is positioned so only half of it is within the joint region). For the second fiber core 1030b, which is partially extended by the bending, the same effect occurs, except that the partial reflection is shifted to longer wavelengths, as illustrated by the third line 1003b.

In cases where the fiber core is not uniformly stressed, the peak of the reflection spectrum is not directly proportional to the strain in the fiber core. Similar effects occur for other partially-bent sections of the fiber. Therefore, if the fiber cannot be placed on the neutral axis of the structure, or otherwise there is not a one-to-one mapping between the sensor regions and the joint regions, the changes in the shape can be used along with the shift in the peak wavelength to better determine the degree of strain in the bent portion of the fiber, and thereby the position of the joint region.

It is understood that the arrangement may vary in other embodiments. For example, the fiber 220 may be fixed to the distal end 218 of the instrument, rather than at the proximal end, as described above. Alternatively, the fiber 220 may be fixed at any known intermediate position. In yet other embodiments, the fiber 220 may be fixed at multiple intermediate and/or end positions. Overall changes in tension caused by stretching or contraction of the fiber 220 could be removed as common-mode noise, similar to a temperature disturbance. In embodiments in which the fiber is fixed at two points, it may be desirable to affix the fiber under tension in the neutral state so that any contraction caused by bending will result in a decrease of the pre-tension, rather than compression of the fiber. In addition, the number, shape, and size of the body segments 212 may vary. For example, fewer or greater joint regions 214 may be provided, thereby increasing the number of body segments 212. In addition, the body segments 212 need not be linear in shape and may include rigid curves or angles.

In accordance with other embodiments of the present invention, one or more of the body segments may comprise a flexible material. In this case, the bending of the instrument 200 is not limited to solely the joint regions 214. Thus, the constraints imposed on the fiber by the flexible structure may be used to model the system. This model may then be inverted either analytically or numerically to derive the instrument's state from the detected set of signals reflected from the Fiber Bragg Gratings. In other words, a forward model is generated that computes the strains expected at the FBG regions from an arbitrary but physically realizable bending of the structure. For example, the stiffness of the flexible section might force it to take the shape of a smooth spline curve when it experiences external forces at the ends and at points along its length, but not allow it to take a right-angle bend in the middle. In the forward model, the input would be the structure's degree of bending at each point, and the output is the predicted strains at the FBG regions. Inverting this model provides another model, this one taking as input the strains at the FBG regions, and providing as output the structure's degree of bending. In some cases this may be done analytically, but for complicated systems, the computation would be done numerically, in real time.

Figure 5:
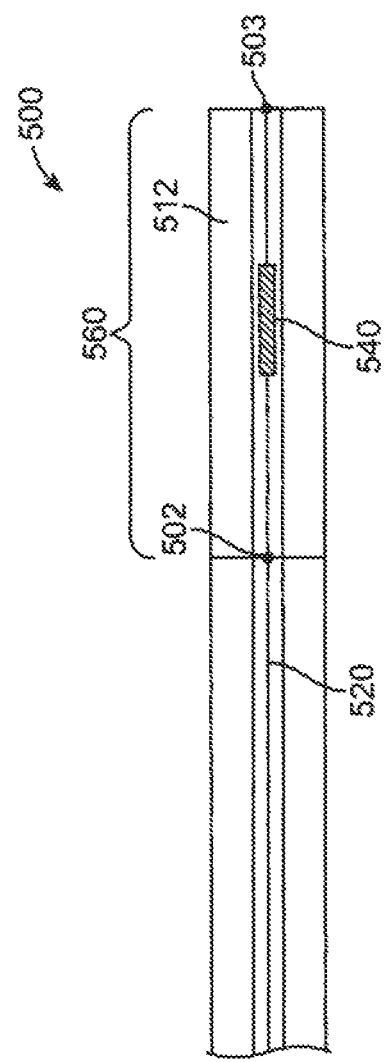
FIG. 5 is a simplified block diagram of another embodiment of the present invention.

FIG. 5 is a simplified block diagram of another embodiment of the present invention in which a surgical instrument 500 is provided having an optical fiber 520, similar to optical fiber 220 described above. In this embodiment, the optical fiber 520 is axially fixed at two anchor points 502-503, with at least one Fiber Bragg Grating sensor region 540 provided between the two fixed anchor points 502-503 to form a fixed axial position region 560. Strain measurements may then be made at this sensor region 540 for a variety of purposes.

For example, the fixed position region 560 of the instrument 500 may be made of a compressible material, such as rubber, or include a compressible portion, such as a torsion spring. Thus, when the distal tip of the instrument 500 is used to apply a force in the axial direction onto a surface, the compressible fixed position region 560 will compress, thereby compressing the fiber 520. The sensor region 540 may be used to detect the axial loading of the fiber 520 in the fixed position region 560, thereby enabling determination of the force applied by the tip of the instrument 500. This determination of force may also include a determination of torque as well.

In other embodiments, the fixed position region 560 is substantially rigid so that no external load is applied to the portion of the fiber 520 in the fixed position region 560. In this case, changes in temperature of the fiber 520 and the rigid section 560 cause thermal expansion or contraction of the fiber 520 and the rigid section 560. Because the fiber 520 is fixed at anchor points 502-503, the net thermal expansion of this composite structure causes strain in the fiber 520. This strain combined with the temperature-induced change in the refractive index causes a shift in the Fiber Bragg Grating's reflection peak, which can then be detected as described above. The temperature may be determined by looking up a detected signal in a pre-calculated lookup table, thereby eliminating the need for comparison with the second sensor region.

In some embodiments, a second sensor region is provided adjacent to the fiber 520 in a second fiber that is not bounded by fixed anchor points. Thus, thermal expansion of the second fiber in this location causes axial movement of the second fiber and does not cause strain in the second fiber. The two fibers are placed close together, so they are at substantially the same temperature. The common-mode signal in each fiber is a function of both the temperature and the strain in each fiber, and since the second fiber is free to move axially, it experiences no strain and thereby provides an output that is a function of temperature only. The shift in the reflected signal from the second fiber can then be subtracted from the shift in the reflected signal from the first fiber, allowing determination of both the temperature and axial strain in region 540 independently.

In yet other embodiments, multiple sensor regions may be provided along the length of the fiber 520, thereby enabling the instrument 500 to be used for multiplexed temperature sensing. In yet other embodiments, the temperature may be measured in the sections of the fiber corresponding to joint regions. The shift in wavelength depends on both the strain in the fiber core, and on the temperature of the fiber core. In the bend-sensitive sections of the fiber, there is no axial strain (which causes a similar wavelength change in all the FBGs in a sensing region, and hence a common-mode signal). In these sections, the bending strain causes opposite shifts in the wavelength of the FBGs on opposite sides of the core, and hence a differential-mode signal. Adding the wavelength shifts for all the FBGs in a single sensitive region thus nulls the bending signal, and amplifies the temperature signal. Thus, the temperature measurement may be accomplished by using the sum of the oppositely disposed cores' readings rather than the difference, as long as there is no axial loading of the fiber.

In these temperature sensing embodiments, it may be desirable for the body segments 512 in the fixed position region 560 to be made of a thermally conductive material, such as a metal, or for at least a portion of the fiber 520 to be exposed to the exterior of the instrument 560 so as to be placed in contact with the target environment for which temperature detection is desired.

In the embodiment shown in FIG. 5, the fixed position region 560 is provided at the distal end of the instrument 500. In other embodiments, one or more fixed position regions 560 including Fiber Bragg Grating sensor regions may be provided at different locations along the length of the instrument 500. These additional sensor regions may be used, e.g., to measure strain at joint regions, as described above with respect to FIGS. 2-4. Thus, the same fiber 520 may be used to both detect bending at the joint regions and force or temperature at the fixed position regions.

In accordance with other embodiments of the present invention, the fiber containing Fiber Bragg Gratings may also be used for other purposes, such as to provide illumination in a body cavity. For example, if the distal end of the fiber is exposed at the distal end of a surgical instrument, such as an endoscope, the fiber may be used to provide illumination for the endoscope. The Fiber Bragg Grating sensors typically operate in a small band in the infrared region of the light spectrum, e.g., 1.55 µm wavelength. In this case, the fiber may also be used to convey light for illumination to the end of the endoscope without interfering with the operation of the strain sensors, as long as the illuminating light is sufficiently removed in wavelength that the illuminating light can be filtered from the infrared light used to interrogate the Fiber Bragg Grating sensors. The illuminating light may be provided in the visible range to directly illuminate a scene.

Figure 6:
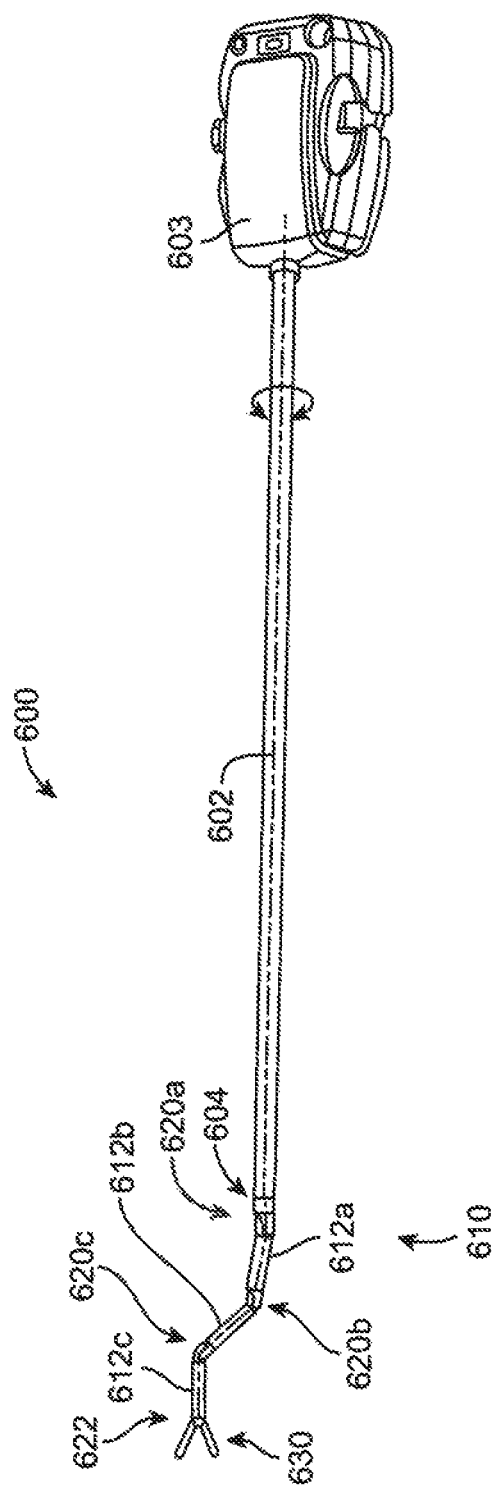
FIG. 6 is a perspective view of a surgical instrument, in accordance with embodiments of the present invention.

FIG. 6 is a perspective view of a surgical instrument 600 in accordance with embodiments of the present invention. This surgical instrument 600 may be used as part of a robotic surgical system, such as the robotic surgical system 2 described above or with the da Vinci Surgical System by Intuitive Surgical, Inc. of Sunnyvale, Calif. A similar robotic manipulator and surgical instrument is described in U.S. Pat. No. 6,902,560, the disclosure of which is incorporated by reference herein in its entirety.

The surgical instrument 600 includes a shaft portion 602, a control housing 603 provided at a proximal end of the shaft portion 602, and a working end 610 at a distal end 604 of the shaft portion 602. The working end 610 comprises three joint assemblies 620a-620c coupling three body segments 612a-612c to the distal end 604 of the shaft portion 602. An end effector 630 is coupled to the third body segment 612c via a wrist assembly 622 at the distal end of the instrument 600. The end effector 630 is the working part of the surgical instrument 600 and can include clamps, jaws, scissors, graspers, needle holders, micro-dissectors, staple appliers, tackers, suction irrigation tools, and clip appliers, and non-articulated tools, such as cutting blades, cautery probes, irrigators, catheters, and suction orifices.

In this embodiment, each of the joint assemblies 620a-620c provides one, two, three, or more degrees of freedom. An optical fiber, such as the fiber 220 described above, may be provided in a channel through the shaft portion 602, the joint assemblies 620a-620c, and the body segments 612a-612c, in order to provide position information regarding the working end 610 and, more particularly, the end effector 630 of the instrument 600. Because the shaft portion 602 is substantially rigid, the position and orientation of the distal end 604 can be determined based on the known position and orientation of the proximal end of the shaft, which is under the control of the manipulator assembly of the robotic system. Therefore, the optical fiber need not be used to determine the position of the shaft portion 602 and Fiber Bragg Gratings need not be provided along the portion of the fiber within the shaft portion 602.

Although it may be possible to estimate the position of the end effector 622 based on the control inputs to the joint assemblies 620a-620c, errors in the estimated position may be introduced due to stretching of the joint actuation cables or other conditions of the driving mechanism. Therefore, sensor regions of the fiber may be provided at each joint assembly 620 in order to determine the extent and orientation of any bending at that joint. This can, in turn, be used to determine the position and orientation of subsequent body segments 612 and ultimately the end effector 630. Roll movement of body segments may be accommodated by providing the sensing fiber in a channel so as to allow rotation of the fiber within the channel. The fiber is quite rigid in torsion, and rotates freely inside the channel, so that roll movement of the body segments would not cause rolling or twisting of the fiber. The extent of rolling may be measured using conventional actuator sensors. This rotational information may then be combined with the information obtained from the bend sensors to determine the orientation of the distal links in space, and to transform the two-dimensional bending determined by the fiber sensor into the degrees of freedom that are actuated at each joint.

In accordance with one aspect of the present invention, the information regarding joint bending obtained from the FBG bend sensors may be used as part of the feedback loop for the control system 250. As described above, actuator sensors may be used to measure the rotation of the motors used to actuate linear movement of the cables, which, in turn, actuates rotational movement of the actively controlled joints. Due to errors introduced by any structures or drivetrain mechanisms that are distal to the actuator sensors, the actual rotation of the joints may not correspond to the rotation measured by the actuator sensors. The bending detected by the bend sensors located in those joints can then be provided back to the servo controller 16 as part of a feedback loop to improve the control of the motors.

Figure 7:
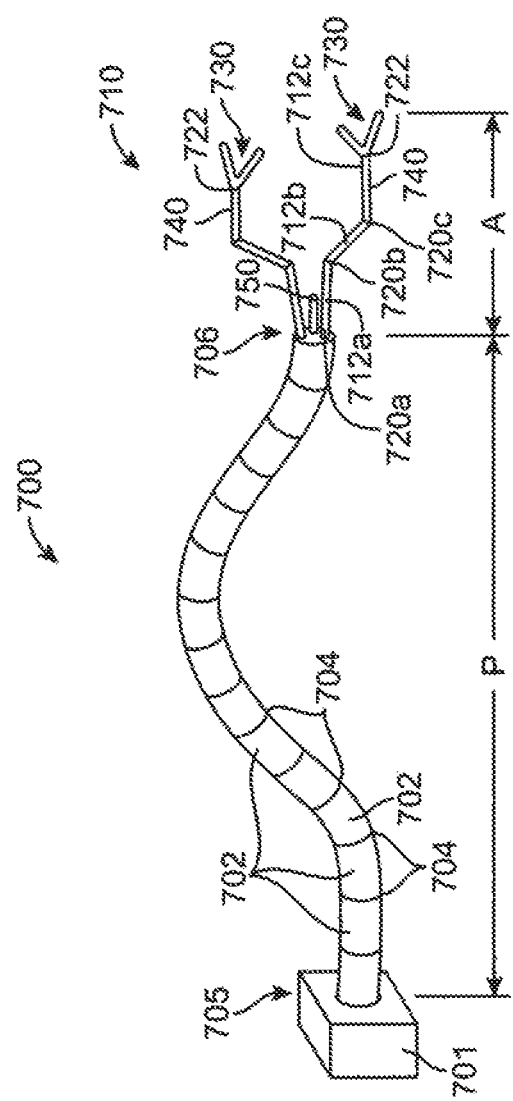
FIG. 7 is a simplified perspective view of a surgical instrument, in accordance with embodiments of the present invention.

In accordance with another aspect of the present invention, FBG sensors may be used in a surgical instrument including both passive and actively-controlled joint regions. FIG. 7 is a simplified perspective view of a surgical instrument 700 in accordance with embodiments of the present invention. The instrument 700 includes a passive region P and an active region A. The passive region P may comprise, e.g., an elongate shaft made of a flexible material and/or an elongate shaft comprising a series of rigid segments 702 coupled by joint regions 704. Similar shafts of rigid segments 702 coupled by joint regions 704 have been used in various endoscopes currently on the market. The shaft in the passive region may be, e.g., approximately 2 m long and 12 mm in diameter. In other embodiments, the dimensions may vary.

Unlike the shaft portion 602 in FIG. 6, the passive region P is not rigid and may bend to facilitate insertion through body passageways and around structures in the patient's body. However, the bending at each joint region 704 is not directly controlled by the operator.

At the distal end 706 of the passive region P is a working end 710, which forms the active region A of the instrument 700. In this embodiment, the working end 710 comprises a pair of actively-controlled robotic arms 740 and an imaging device (e.g., a camera 750). In other embodiments, the working end 710 may have greater or fewer components. For example, the working end 710 may include only a single arm 740 or three or more arms 740, and the imaging device may be omitted.

Each of the robotic arms 740 may be similar in operation to the working end 610 described above with respect to FIG. 6. Each arm 740 comprises three joint assemblies 720a-720c coupling three body segments 712a-712c to the distal end 706 of the passive region P. An end effector 730 is coupled to the third body segment 712c via a wrist assembly 722 at the distal end of the instrument 700. As with instrument 600, each of the joint assemblies 720a-720c may provide one, two, three, or more degrees of freedom.

The instrument 700 may be inserted into a patient's body and controlled using a robotic surgical system similar to the robotic surgical system 2 shown in FIG. 1. In this case, only a single manipulator assembly may be used to control the single instrument 700. In other cases, multiple manipulator assemblies may be used to control other instruments.

As with the surgical system 2 described above, the movement of each joint assembly 720a-720c may be actuated by motors controlled by a servo controller (not shown). The motors may be coupled to the joint assemblies 720a-720c using, e.g., actuation cables. In instrument 600, the shaft 602 is rigid and linear, so the joint assemblies 620a-620c may be actuated using a combination of rigid shafts and cables made of a stiff material, such as, e.g., tungsten. In contrast, in instrument 700, the working end 710 is separated from the proximal end 705 of the instrument 700 by a flexible region. As a result, rigid shafts cannot be used to transmit the actuation force, and stiff cables may unacceptably limit the bending of the passive region P and experience high frictional forces when being linearly translated through a curved path. Thus, the actuation cables may comprise a less rigid material, such as a polymer or composite.

Although a polymer cable may not experience as much friction as a tungsten cable when passed through a channel in the passive region P, the polymer cable may experience significantly increased stretching, thereby increasing the difficulty of measuring the position of each joint assembly 720a-720c based on measurements of the actuator sensors. In addition, because the passive region P is not directly controlled by the operator, it is difficult for the operator to accurately determine the position and orientation of the distal end 706 inside of the patient's body. Thus, even if the positions of each joint assembly 720a-720c were capable of being accurately measured, the position and orientation of the end effectors 730 would only be known relative to the position and orientation of the distal end 706. Thus, the position and orientation of the end effectors 730 relative to an external coordinate system (e.g., defined by base 701 in a known location outside of the patient's body) will also be indeterminable.

In accordance with embodiments of the present invention, a multi-core optical fiber, such as the fiber 220 described above, may be provided in a channel through the passive region P and/or the active region A, in order to provide position information of the instrument 700, as described above. In one embodiment, the fiber may be provided only in passive region P, so that the position and orientation of the distal end 706 can be determined relative to the external coordinate system. The position and orientation of the end effectors 730 relative to the distal end 706 can then be determined based on the measurements by the actuator sensors.

In another embodiment, the fiber including FBG bend sensors may be provided only in the active region A. The position and orientation of the distal end 706 of the passive region P may be determined using any of the conventional methods described above. In this case, the position and orientation of each individual segment along the length of the passive region P may be irrelevant, so long as the position and orientation of the distal end 706 is known. Thus, it may be possible to use an external detection system to determine the position and orientation of the distal end 706. The FBG sensors in the fiber can then be used to determine the position and orientation of each joint assembly 720a-720c in the arms 740. This information can be combined with the externally detected position of the distal end 706 to provide accurate position and orientation information regarding the end effectors 730.

In yet another embodiment, the fiber including FBG bend sensors may be provided along the entire length of the instrument 700. Thus, the position and orientation along the entire length of the instrument 700 can be determined relative to an external coordinate system.

This position and orientation information can be used for a variety of purposes. For instance, the operator may utilize the determined position of the end effectors 730 in order to navigate to a site of interest in the patient's body. Alternatively, the control system may utilize this information as part of a feedback loop.

Figure 8:
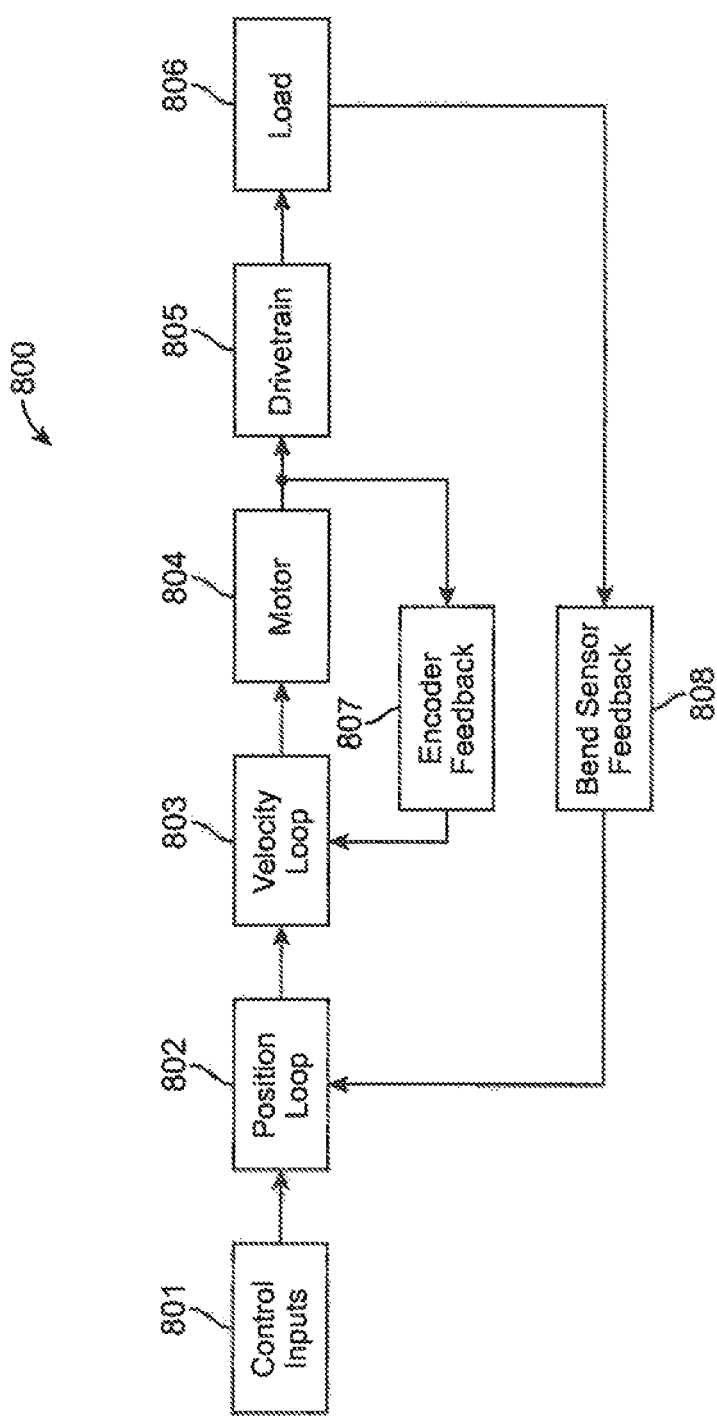
FIG. 8 is a simplified block diagram illustrating a multi-input feedback loop, in accordance with embodiments of the present invention.

FIG. 8 is a simplified block diagram illustrating a dual loop control, multi-input/single output feedback loop 800 in accordance with embodiments of the present invention. The dual-loop control includes control inputs 801 and utilizes two feedback sources, the actuator sensor feedback 807 and the feedback 808 from the bend sensors in the joint assemblies, to compensate for accuracy problems that arise from errors occurring between motor 804 and load 806. The actuator sensor feedback 807 is used to close the velocity loop 803 and the bend sensor feedback 808 is used to close the position loop 802.

Because the load 806 is connected to the motor 804 through the drivetrain 805 which is necessarily compliant, the load 806 does not react immediately to changes in motor position. The time lag between motor rotation and load movement can make the load feedback too slow to close the velocity loop 803. In a simple case, one solution is to connect the bend sensor, which directly senses the load, to the slower position loop 802 (where accuracy is most important), and to connect the actuator sensor to the faster velocity loop 803 (where responsiveness is most important). In other cases, the dual loop feedback may utilize more complex algorithms for mixing the two sensor signals. In addition, unmodeled friction in the drivetrain can make the position and velocity of the load a poor indicator of the position and velocity of the motor, and thus inappropriate for use as an actuator sensor.

In accordance with other aspects of the present invention, FBG sensors may be used to locate a portion of a surgical instrument (e.g., the tip of the instrument) in a fixed external coordinate system in order to combine external data (such as image data from a magnetic resonance imaging (MRI) or ultrasound imaging system) with the positioning information to assist the operator in performing the surgical procedure.

For example, the detection system 260 may be coupled to the imaging system 270 to provide real-time position information for use in the control of the instrument 200. The imaging system 270 may include image data of the patient from an external source, such as a pre-operative MRI. The proximal end of the instrument 200 can then be supported by the surgical system 2 in a known position relative to the patient. Thus, one end of the sensing fiber may have a fixed position and angular orientation in a coordinate system external to the patient. For example, in a surgical robot, the proximal end of the fiber may be fixed to the frame holding the apparatus, which would be fixed in position relative to the patient during a period of use. As described above, the detection system 260 can then utilize the FBG sensors to determine the angles of all the joint regions in the instrument, including those that are not actively controlled. This information can then be combined with the known lengths of the structure's links to determine the position and orientation of each portion of the instrument.

A calibration step may be used, depending on whether the external data to be merged is available in the coordinate system of the frame that holds the fixed end of the fiber. In some cases (such as for pre-operative MRI images), the image data will be referenced to landmarks of patient anatomy. The image data can be aligned by identifying three patient landmarks that are visible in the external data with the robotic camera, and viewing these from two different angles. The landmarks may be internal or external anatomical features, or fiducials placed prior to imaging.

The sensor system, by providing in three dimensions unambiguous position and orientation information for each link in the instrument, enables this coordinate mapping for all parts of the instrument. This takes advantage of the ability of the OFDR interrogation system to multiplex many FBG sensors along a single fiber. In addition to the image registration described above, this allows the system to provide a richer set of features to the user. For example, the position of tools or other structure elements that are not currently in the field of view of a camera can be determined, and indicated to the user, and these features can be provided more easily across a wide range of minimally invasive surgery platforms with different architectures.

In some embodiments, the position information can be combined with the external image data to provide the operator with an image showing the location of the tip of the instrument on the MRI image in order to provide additional context for the surgical procedure.

In accordance with other embodiments, the external data may be combined with the image produced by a camera carried on the surgical instrument, such as, e.g., camera 750 in FIG. 7. If the surgical system is one in which the camera is part of the same structure as the manipulators (as in the flexible "snake-like" instrument shown in FIG. 7), then the same position data used to provide enhanced feedback control of the robotic arms 740 can also be used to determine the position of the camera 750. This data can be combined with other data on the orientation of the proximal end 705 of the fiber (anchored to the instrument's mounting structure) relative to the patient, to determine the location and orientation of the endoscopic camera 750 with respect to the patient. Once this is known, the MRI or other data, which is available in a coordinate system referenced to the patient, can be superimposed on the camera image, or displayed alongside it, viewed from the same point as the camera image. If the camera 750 is controlled on a separate robotic arm, a fiber sensor of the type described above can be added to the robotic arm to enable these operations.

In accordance with other embodiments of the present invention, FBG bend sensors in a surgical instrument may be used for calibration purposes in order to correct for manufacturing defects. These manufacturing defects may affect the dimensions and control of the various components of a surgical instrument, thereby causing the end effector and any intermediate components to be located in a position other than the assumed ideal. In order to calibrate the device, the control system will attempt to position the instrument in one or more known configurations. The FBG bend sensors in the instrument may be used to compare the measured position of the instrument to the expected position of the instrument. Any differences between the measured position and the expected position can be then be compensated for by the controller software.

The sensing of the position and orientation of the distal end of a surgical instrument enables the performance of a system identification on each device's actual kinematics, mapping out errors (e.g., differences from the ideal kinematics, such as those induced by manufacturing or material variation) automatically, and storing this error map in non-volatile memory on the device. Thus, the accuracy of the device can be improved. This mapping might occur once in the factory, or might occur each time the device is used. The latter would allow for correction of errors induced by aging or autoclave cycles, or any other time-dependent cause.

Figure 9:
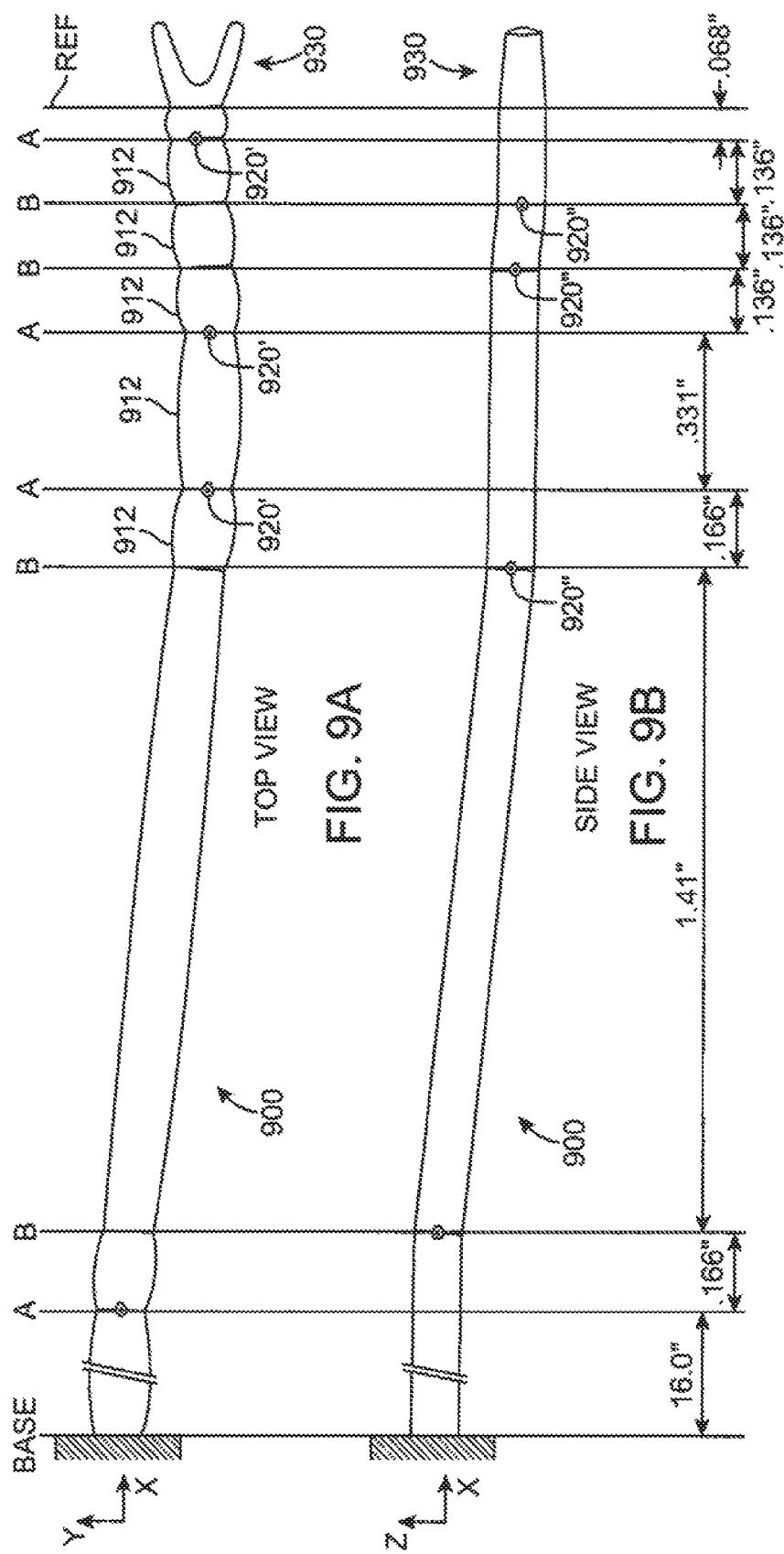
FIGS. 9A-9B are simplified block diagrams illustrating top and side views of a portion of a surgical instrument, in accordance with embodiments of the present invention.

FIGS. 9A-9B are simplified block diagrams illustrating top and side views of a portion of a surgical instrument 900, in accordance with other embodiments of the present invention. The surgical instrument 900 comprises a plurality of rigid links 912 coupled by a plurality of joint regions 920 having an end effector 930 provided at the distal end. In some cases (as in the embodiment shown in FIGS. 9A-9B), the proximal end of the instrument 900 may be mounted to a fixed base. In other cases, the proximal end of the instrument 900 may be mounted to a distal end of an arm, such as the shaft portion 602 shown in FIG. 6. In this embodiment, each joint region enables passive bending in one plane. For example, the joint regions 920' (marked "A") allow rotation about an axis in the z-direction, and the joint regions 920" (marked "B") allow rotation about an axis in the y-direction. Each of the joint regions 920' and 920" allows a range of motion of, e.g., ±45°. A plurality of optical fiber cores including at least one Fiber Bragg Grating region are provided in the instrument 900. The fiber cores may be part of a single optical fiber anchored to the base and passed through the neutral axis of the instrument 900. The FBG regions in the fiber cores may be used to determine the position and orientation of the instrument 900, similar to the embodiments described above.

Embodiments of the present invention may provide various advantages not provided by prior art systems. For example, embodiments may enable more precise control of the elements located at the distal end of a robotically-controlled surgical instrument. In other embodiments, precise positioning and control may be achieved of a robotically-controlled surgical instrument having unactuated or flexible bends or joints.

In some embodiments, the cross-sectional area of the surgical instrument may be reduced because a single fiber can be used for multiple purposes, including sensing the position of all of the joints in the structure, sensing the forces applied to the structure, sensing temperature, and providing illumination for an imaging system. This may have particular applicability for endoscopes having a limited number of working ports.

In some embodiments, the angles of each of the joints or flexible portions of the surgical instrument may be mapped in real time. This can enable precise transformation of the location coordinate system at the instruments end effector to a global coordinate system. This transformation may enable the combination of data and images acquired by other systems with data acquired by the surgical system, such as, e.g., images obtained from endoscopic cameras mounted on the end effector.

In addition, by determining the position and orientation of the segments of the surgical instrument in a world reference frame, a flexible robotic surgery system can more completely mimic the operation of pre-existing minimally-invasive surgical systems that are designed to provide this information, such as, the da Vinci Surgical System, providing the ability to re-use user features and the code base developed for those systems. Thus a consistent surgeon experience can be provided, independent of the robot system architecture.

While the invention has been described in terms of particular embodiments and illustrative figures, those of ordinary skill in the art will recognize that the invention is not limited to the embodiments or figures described. For example, the position In many of the embodiments described above, the optical fiber comprises a single fiber having multiple cores. In other embodiments, the multiple single-core optical fibers may be used.

Embodiments described above include the use of actuator sensors for detecting movement of the actuators. In various embodiments, the actuator sensors may detect one or more of the position, velocity, acceleration, and applied force of the actuators. It will be understood that the detected applied force may be an applied torque, and the detected velocity and acceleration may be an angular velocity and angular acceleration. In addition, the sensed information provided by the actuator sensors to the control system may be provided in various forms and need not be limited to a direct measurement of position, velocity, acceleration, and applied force. For example, the actuation sensor may provide a logarithm of position to the control system, which, in turn, converts that value into a position.

In addition, the robotic surgical system described above may utilize cables in tension in order to actuate movement of the surgical instrument. In other embodiments, other actuation mechanisms, such as rods or tubes in compression and torsion, may be used to actuate movement. In addition, the FBG sensors may be used to detect the bending of passive joints as well. Some embodiments may have particular applicability for systems utilizing hydraulic or pneumatic mechanisms to actuate movement. Although hydraulic and pneumatic mechanisms are not subject to the frictional forces afflicting cables or tubes, these mechanisms introduce other control problems. For instance, in order to utilize hydraulics or pneumatics to transmit actuation forces through a flexible or multi-jointed structure having multiple degrees of freedom, very small cylinders that may not be completely sealed are used. The use of such small cylinders may result in a drift in the expected position of the actuator. Having real-time position feedback of the positions of the hydraulically or pneumatically actuated joints would ameliorate this problem.

In addition, the anchoring of the optical fiber cores relative to the instrument body may be accomplished in a variety of ways. For example, the optical fiber may be attached to an interior surface of the channel passing through the instrument. Alternatively, the optical fiber may be attached to a structure external to the robotic arm, but at a fixed position relative to the arm.

Therefore, it should be understood that the invention can be practiced with modification and alteration within the spirit and scope of the appended claims. The description is not intended to be exhaustive or to limit the invention to the precise form disclosed. It should be understood that the invention can be practiced with modification and alteration and that the invention be limited only by the claims and the equivalents thereof.

What is claimed is:

1. An apparatus comprising:
a robotic manipulator; and
a surgical instrument mounted to the robotic manipulator, the surgical instrument comprising:
an elongate arm comprising:
an actively controlled bendable region including at least one joint region and an end effector,
a passively bendable region including a distal end coupled to the actively controlled bendable region,
an actuation mechanism extending through the passively bendable region and coupled to the at least one joint region to control the actively controlled bendable region, and
a channel extending through the elongate arm; and
an optical fiber positioned in the channel, wherein the optical fiber includes an optical fiber bend sensor in at least one of the passively bendable region or the actively controlled bendable region.

2. The apparatus of claim 1, wherein the optical fiber bend sensor comprises a plurality of optical fiber cores in the optical fiber.

3. The apparatus of claim 1, wherein the optical fiber bend sensor comprises a plurality of optical fiber cores in the optical fiber, and each of the plurality of optical fiber cores comprises a Fiber Bragg Grating (FBG) region.

4. The apparatus of claim 1, further comprising:
a detection system, coupled to the optical fiber bend sensor, comprising:
a light source, wherein the light source is configured to provide light to the optical fiber bend sensor; and
a light detector, wherein the light detector is configured to receive a reflectance spectrum from the optical fiber bend sensor.

5. The apparatus of claim 4, further comprising:
a control system comprising a servo controller,
wherein the control system is configured to command a bend in the at least one joint region, and
wherein the control system is configured to receive sensed information from the detection system.

6. The apparatus of claim 5, wherein the control system is configured to use the sensed information to compensate elongate arm position information for bending of the passively bendable region.

7. The apparatus of claim 5:
wherein the control system further comprises a display system, and
wherein the control system is configured to combine image data relative to a fixed external coordinate system with position information from the detection system to display the image data relative to a coordinate system associated with the elongate arm.

8. The apparatus of claim 7, further comprising:
an imaging device positioned on the elongate arm,
wherein the control system is configured to display a first image including a second image from the imaging device and the image data, and
wherein the first image is displayed relative to a coordinate system associated with the second image from the imaging device.

9. The apparatus of claim 5, further comprising:
an imaging device positioned on the elongate arm,
wherein the control system comprises a display system configured to display an image from the imaging device and to display a position of the imaging device based on detected light reflected by or transmitted through the optical fiber bend sensor.

10. The apparatus of claim 9:
wherein the control system comprises a control input device configured to receive control input from a user,
wherein the control input device is coupled to the surgical instrument to command movement of the surgical instrument in at least one-degree of freedom in response to the control input from the user,
wherein the control input device is configured to provide feedback to the user regarding at least one of a position of the elongate arm or an applied force of the elongate arm, and
wherein the feedback is based on sensed information received by the control system from the detection system.

11. The apparatus of claim 1, wherein the optical fiber bend sensor comprises a single optical fiber including a plurality of optical fiber cores.

12. The apparatus of claim 11, wherein a longitudinal axis of the channel is a substantially neutral bending axis of the elongate arm.

13. The apparatus of claim 1, wherein the optical fiber comprises a plurality of optical fiber cores axially attached to the channel at least at two points along the channel.

14. The apparatus of claim 1:
wherein the optical fiber bend sensor comprises at least one Fiber Bragg Grating (FBG) region; and
wherein the apparatus further comprises a detection system configured to determine an applied force of the at least one joint region of the elongate arm based on detected light reflected by or transmitted through the at least one FBG region.

15. The apparatus of claim 1, further comprising:
an actuator sensor, wherein the actuator sensor is configured to detect movement of the actuation mechanism,
wherein a control system is configured to receive and to use sensed information from a detection system coupled to the optical fiber and sensed information from the actuator sensor as feedback sources.

16. An apparatus comprising:
a robotic manipulator; and
a surgical instrument mounted to the robotic manipulator, the surgical instrument comprising:
an elongate arm comprising:
an actively controlled bendable region including at least one joint region and an end effector,
a passively bendable region including a distal end coupled to the actively controlled bendable region,
an actuation mechanism extending through the passively bendable region and coupled to the at least one joint region to control the actively controlled bendable region, and a channel extending through the elongate arm; and an optical fiber positioned in the channel, wherein the optical fiber includes an optical fiber bend sensor in at least one of the passively bendable region or the actively controlled bendable region, wherein the optical fiber comprises a plurality of optical fiber cores, and each of the plurality of optical fiber cores comprises a plurality of Fiber Bragg Grating (FBG) regions, and wherein the optical fiber bend sensor includes:
   a first bend sensor region including at least one of the plurality of FBG regions in the passively bendable region; and
   a second bend sensor region including at least one of the plurality of FBG regions in the actively controlled bendable region.

17. The apparatus of claim 16:

wherein the actively controlled bendable region includes a plurality of joint regions, wherein the plurality of joint regions includes the at least one joint region, wherein the optical fiber comprises a plurality of optical fiber cores, and each of the plurality of optical fiber cores comprises a plurality of Fiber Bragg Grating (FBG) regions, wherein the optical fiber bend sensor comprises a plurality of bend sensor regions, and wherein each of the plurality of bend sensor regions comprises one of the plurality of FBG regions positioned to correspond to one of the plurality of joint regions.

18. The apparatus of claim 17:

wherein the plurality of optical fiber cores are anchored to an anchor point fixed relative to the elongate arm; and wherein each of the plurality of FBG regions has a length longer than a length of the corresponding one of the plurality of joint regions such that the apparatus is configured to allow the FBG regions to detect bending of the corresponding one of the plurality of joint regions, despite axial movement of the optical fiber cores relative to the elongate arm caused by bending of one or more of the plurality of joint regions.

19. The apparatus of claim 17, further comprising:

a detection system coupled to the optical fiber, wherein the detection system is configured to measure a shape of a spectrum of detected light from each of the plurality of FBG regions.

20. The apparatus of claim 17, further comprising:

a detection system coupled to the optical fiber, wherein the detection system is configured to measure a shift in wavelength of detected light from each of the plurality of FBG regions.

* * * * *